(12) United States Patent
Wolfe et al.

(10) Patent No.: US 6,696,488 B2
(45) Date of Patent: Feb. 24, 2004

(54) (HYDROXYETHYL)UREAS AS INHIBITORS OF ALZHEIMER'S β-AMYLOID PRODUCTION

(75) Inventors: Michael S. Wolfe, Newton, MA (US); Dennis J. Selkoe, Brookline, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 09/927,913

(22) Filed: Aug. 10, 2001

(65) Prior Publication Data

US 2002/0111365 A1 Aug. 15, 2002

Related U.S. Application Data

(60) Provisional application No. 60/225,043, filed on Aug. 11, 2000.

(51) Int. Cl.$^7$ ............................................... A61K 31/27
(52) U.S. Cl. ........................ 514/485; 514/314; 514/487; 514/478; 514/595; 514/596
(58) Field of Search ................................ 514/478, 595, 514/596, 314, 485, 487; 560/32, 24, 158; 564/47, 48, 56; 544/176

(56) References Cited

U.S. PATENT DOCUMENTS

| | | |
|---|---|---|
| 2,331,926 A | 10/1943 | Olin |
| 2,344,259 A | 3/1944 | Morgan et al. |
| 3,854,480 A | 12/1974 | Zaffaroni |
| 4,452,775 A | 6/1984 | Kent |
| 4,599,198 A | 7/1986 | Hoover |
| 4,757,050 A | 7/1988 | Natarajan et al. |
| 5,039,660 A | 8/1991 | Leonard et al. |
| 5,475,013 A | 12/1995 | Talley et al. |
| 5,604,198 A | 2/1997 | Poduslo et al. |
| 5,698,569 A | 12/1997 | Talley et al. |
| 5,703,129 A | 12/1997 | Felsenstein et al. |
| 5,827,819 A | 10/1998 | Yatvin et al. |
| 5,830,897 A | 11/1998 | Vasquez et al. |
| 5,872,101 A | 2/1999 | Munoz et al. |
| 5,919,815 A | 7/1999 | Bradley et al. |
| 5,955,459 A | 9/1999 | Bradley et al. |
| 5,977,086 A | 11/1999 | Lisziewicz et al. |
| 5,977,174 A | 11/1999 | Bradley et al. |
| 5,990,092 A | 11/1999 | Walsh |
| 6,100,277 A | 8/2000 | Tucker et al. |

FOREIGN PATENT DOCUMENTS

| | | |
|---|---|---|
| AU | 79823/87 | 4/1988 |
| DE | 3643977 A1 | 7/1987 |
| DE | 3635907 A1 | 4/1988 |
| GB | 1046045 | 10/1966 |
| WO | 92/08698 A1 | 5/1992 |
| WO | WO00/56335 A1 | 9/2000 |
| WO | 01/66564 A2 | 9/2001 |
| WO | 02/02518 A2 | 1/2002 |

OTHER PUBLICATIONS

Chase BH et al., The synthesis of some potential antibacterial agents, *J. Pharm Pharmacol*, 1964, 16:163–173.
Johnston TP et al., Synthesis of potential anticancer agents. 38. N–Nitrosoureas. Further synthesis and evaluation of haloethyl derivatives, *J Med Chem*, 1971, 14(7):600–614.
Kick EK et al., Structure–based design and combinatorial chemistry yield low nanomolar inhibitors of cathepsin D, *Chem Biol*, 1997, 4(4):297–307.
Argarwal NS et al., *J Med Chem* 29:2519–24 (1986).
Bryant M et al., *Antimicrob Agents Chemother* 39:2229–34 (1995).
Capobianco AJ et al., *Mol Cell Biol* 17:6265–73 (1997).
Citron M et al., *Proc Natl Acad Sci USA* 93:13170–5 (1996).
De Strooper B et al., *Nature* 398:518–22 (1999).
Deftos ML et al., *Curr Opin Immunol* 12:166–72 (2000).
Getman DP et al., *J Med Chem* 36:288–91 (1993).
Hardy J, *Proc Natl Acad Sci USA* 94:2095–7 (1997).
Huff JR, *J Med Chem* 34:2305–14 (1991).
Iwatsubo T et al., *Neuron* 13:45–53 (1994).
Jarrett JT et al., *Biochemistry* 32:4693–7 (1993).
Jeffries S et al., *Mol Cell Biol* 20:3928–41 (2000).
Johnson–Wood K et al., *Proc Natl Acad Sci USA* 94:1550–5 (1997).
Kati WM et al., *Biochemistry* 26:7621–6 (1987).
Leung D et al., *J Med Chem* 43:305–41 (2000).
Li YM et al., *Nature* 405:689–94 (2000).
Li YM et al., *Proc Natl Acad Sci USA* 97:6138–43 (2000).
Luly JR et al., *J Org Chem* 52:1487–92 (1987).
Roher AE et al., *Proc Natl Acad Sci USA* 90:10836–40 (1993).
Ruchoux MM et al., *J Neuropathol Exp Neurol* 56:947–64 (1997).
Schroeter EH et al., *Nature* 393:382–6 (1998).
Selkoe DJ, *Annu Rev Cell Biol* 10:373–403 (1994).
Selkoe DJ, *Curr Opin Neurobiol* 10:50–7 (2000).
Selkoe DJ, *Science* 275:630–1 (1997).
Seubert P et al., *Nature* 359:325–7 (1992).
Shearman MS et al., *Biochemistry* 30:8698–704 (2000).
Smidt ML et al., *Antimicrob Agents Chemother* 41:515–22 (1997).
Vassar R et al., *Science* 286:735–41 (1999).
Wolfe MS et al., (Hydroxyethyl)urea–containing peptidomimetics: new molecular probes for gamma–secretase/presenilin. Abstract, Society for Neuroscience Annual Meeting, New Orleans, Nov. 4–9, 2000.
Wolfe MS et al., *Biochemistry* 38:4720–7 (1999).
Xia W et al., *J Biol Chem* 272:7977–82 (1997).
Zagouras P et al., *Proc Natl Acad Sci USA* 92:6414–8 (1995).

*Primary Examiner*—Shailendra Kumar
(74) *Attorney, Agent, or Firm*—Wolf, Greenfield and Sacks, P.C.

(57) ABSTRACT

Novel (hydroxyethyl)ureas are described. These compounds are effective inhibitors of certain aspartyl proteases, notably secretases involved in the enzymatic cleavage of amyloid precursor protein (APP) to yield amyloid-β peptide. Methods are provided for administering the novel compounds to treat β-amyloid-associated diseases, notably Alzheimer's disease.

3 Claims, 2 Drawing Sheets

(HYDROXYETHYL)UREAS AS INHIBITORS OF ALZHEIMER'S β-AMYLOID PRODUCTION

RELATED APPLICATION

This application claims priority to U.S. Provisional Patent Application No. 60/225,043, filed Aug. 11, 2000, the entire contents of which are hereby incorporated by reference.

GOVERNMENT RIGHTS

This invention was funded in part under National Institute of Health Grant No. NS37537. The government may retain certain rights in these inventions.

FIELD OF THE INVENTION

The invention relates to methods and compositions for inhibiting certain aspartyl proteases. More particularly it relates to methods and compounds for inhibiting the enzymatic activity of secretases involved in converting amyloid precursor protein to amyloid-β peptide. The methods and compounds of the invention can be used in the treatment of neurodegenerative disorders, notably Alzheimer's disease.

BACKGROUND OF THE INVENTION

Accumulating biochemical, histological, and genetic evidence supports the hypothesis that the 4 kDa β-amyloid protein (Aβ) is an essential component in the pathogenesis of Alzheimer's disease (AD). Selkoe D J, *Science* 275:630–631 (1997). Hardy *J, Proc Natl Acad Sci USA* 94:2095–2097 (1997). Despite the intense interest in the role of Aβ in the etiology of AD, the molecular mechanism of Aβ biosynthesis is poorly understood. The 39-43-residue Aβ is formed via the sequential cleavage of the integral membrane amyloid precursor protein (APP) by β- and γ-secretases. Selkoe D J, *Annu Rev Cell Biol* 10:373–403 (1994). β-Secretase cleavage of APP occurs near the membrane, producing the soluble $APP_s$-β and a 12 kDa C-terminal membrane-associated fragment (CTF). The latter is processed by γ-secretase, which cleaves within the transmembrane domain of the substrate to generate Aβ. An alternative proteolytic event carried out by α-secretase occurs within the Aβ portion of APP, releasing $APP_s$-α, and subsequent processing of the resulting membrane-bound 10 kDa CTF by γ-secretase leads to the formation of a 3 kDa N-terminally truncated version of Aβ called p3.

Heterogeneous proteolysis of the 12 kDa CTF by γ-secretase generates primarily two C-terminal variants of Aβ, 40- and 42-amino acid versions ($Aβ_{40}$ and $Aβ_{42}$), and parallel processing of the 10 kDa CTF generates the corresponding C-terminal variants of p3. Although $Aβ_{42}$ represents only about 10% of secreted Aβ, this longer and more hydrophobic variant is disproportionally present in the amyloid plaques observed post mortem in AD patients (Roher A E et al., *Proc Natl Acad Sci USA* 90:10836–40 (1993); Iwatsubo T et al., *Neuron* 13:45–53 (1994)), consistent with in vitro studies illustrating the kinetic insolubility of $Aβ_{42}$ vis-á-vis $Aβ_{40}$. Jarrett J T et al., *Biochemistry* 32:4693–4697 (1993). Importantly, all genetic mutations associated with early-onset (<60 years) familial Alzheimer's disease (FAD) result in increased $Aβ_{42}$ production. Selkoe D J, *Science* 275:630–631 (1997); Hardy J, *Proc Natl Acad Sci USA* 94:2095–2097 (1997). An understanding of the production of Aβ in general and that of $Aβ_{42}$ in particular is essential for elucidating the molecular mechanism of AD pathogenesis and may also lead to the development of new chemotherapeutic agents which strike at the etiological heart of the disease.

Both γ-secretase and β-secretase are attractive targets for inhibitor design for the purpose of inhibiting production of Aβ. While γ-secretase is an attractive target for inhibitor design, little is known about the structure, mechanism, or binding requirements of this unidentified protease.

In view of the foregoing, a need still exists to develop compositions and methods for treating disorders characterized by the production and deposition of β-amyloid.

SUMMARY OF THE INVENTION

The present invention relates to novel compounds useful for inhibiting certain aspartyl proteases, particularly those involved in generating β-amyloid from APP. The compounds are useful for treating a subject having or at risk of having a β-amyloid-associated disease.

In a first aspect, the invention provides novel compounds of Formula I

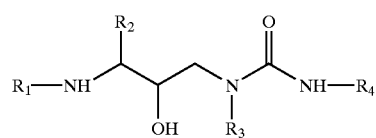

Formula I wherein $R_1$ is selected from the group consisting of hydrogen, alkyl, cycloalkyl, aromatic, heteroaromatic, $R_6O$ (C=O), and $R_7R_8N$(C=O), wherein $R_6$, $R_7$, and $R_8$ are independently selected from the group consisting of hydrogen, alkyl, cycloalkyl, aromatic, and heteroaromatic, provided $R_1$ is not bonded to the Formula I nitrogen via a group

wherein Z is C and X is O, S, or N; $R_2$ and $R_3$ are each independently selected from the group consisting of hydrogen, alkyl, cycloalkyl, aromatic, and heteroaromatic; $NH-R_4$ is peptidyl or $R_4$ is independently selected from the group consisting of hydrogen, alkyl, cycloalkyl, aromatic, and heteroaromatic; and non-hydrogen $R_1$, $R_2$, $R_3$, $R_4$, $R_6$, $R_7$, and $R_8$ can independently be substituted with alkylamino, alkoxy, amino, halide, nitro, sulfate, sulfonamide, sulfoxide, or thiol ether.

In some preferred embodiments $R_1$ is t-butyloxycarbonyl (Boc).

In these and other preferred embodiments $R_2$ is bulky and is selected from the group consisting of cyclohexyl, benzyl and other amino acid side chains. In a more preferred embodiment $R_2$ is benzyl, i.e., the side chain of phenylalanine.

In these and other preferred embodiments $R_3$ is selected from the group consisting of methyl, isopropyl, isobutyl, benzyl and other amino acid side chains. In a more preferred embodiment $R_3$ is benzyl, i.e., the side chain of phenylalanine. Also in these and other preferred embodiments $R_3$ is selected from the group consisting of the side chains of alanine, leucine, and valine.

In these and other preferred embodiments $NH-R_4$ is selected from the group consisting of alanine-phenylalanine O-methyl ester, leucine-alanine O-methyl ester, leucine—leucine O-methyl ester, leucine-phenylalanine O-methyl ester, leucine-valine O-methyl ester, and valine-phenylalanine O-methyl ester. In some preferred embodiments NH—R$_4$ is selected from the group consisting of leucine-valine-alanine O-methyl ester, leucine-valine-leucine O-methyl ester, leucine-valine-phenylalanine O-methyl ester, and leucine-valine—valine O-methyl ester.

In one particularly preferred embodiment R$_1$ is t-butyloxycarbonyl; R$_2$ is benzyl; R$_3$ is benzyl; and NH—R$_4$ is leucine—leucine O-methyl ester.

In another particularly preferred embodiment R$_1$ is t-butyloxycarbonyl; R$_2$ is benzyl; R$_3$ is isobutyl; and NH—R$_4$ is leucine—leucine O-methyl ester.

In another particularly preferred embodiment R$_1$ is t-butyloxycarbonyl; R$_2$ is benzyl; R$_3$ is benzyl; and NH—R$_4$ is alanine-phenylalanine O-methyl ester.

In another particularly preferred embodiment R$_1$ is t-butyloxycarbonyl; R$_2$ is benzyl; R$_3$ is benzyl; and NH—R$_4$ is leucine-valine O-methyl ester.

In another particularly preferred embodiment R$_1$ is t-butyloxycarbonyl; R$_2$ is benzyl; R$_3$ is benzyl; and NH—R$_4$ is valine-phenylalanine O-methyl ester.

In another particularly preferred embodiment R$_1$ is t-butyloxycarbonyl; R$_2$ is benzyl; R$_3$ is benzyl; and NH—R$_4$ is leucine-valine-phenylalanine O-methyl ester.

According to this aspect of the invention, certain embodiments embrace a stereoisomer of the compound of Formula I. Other related embodiments embrace a mixture of different stereoisomers of the compound of Formula I. In certain preferred embodiments all stereocenters are R.

Yet another embodiment is a pharmaceutically acceptable salt of the compound of Formula I.

Also provided according to this aspect of the invention is a pharmaceutical composition comprising a compound of Formula I and further comprising a pharmaceutically acceptable carrier. Preferably the pharmaceutically acceptable carrier is adapted for oral administration of a compound of Formula I to a subject. More preferably the pharmaceutically acceptable carrier is adapted for promoting delivery of a compound of Formula I to a brain of a subject.

The invention also provides a method for making a pharmaceutical composition. The method comprises placing a compound of Formula I according to this aspect of the invention in a pharmaceutically acceptable carrier. The method specifically embraces placing the above-identified preferred embodiments of the compound of Formula I in a pharmaceutically acceptable carrier.

In a second aspect the invention provides novel compounds of Formula I

Formula I

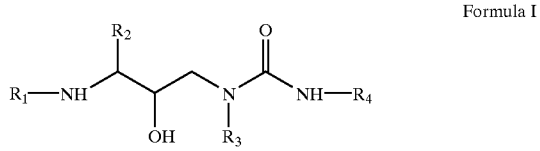

wherein R$_1$ is selected from the group consisting of hydrogen, alkyl, cycloalkyl, aromatic, heteroaromatic, acyl (R$_5$C=O), R$_6$(C=O), and R$_7$R$_8$N(C=O), wherein R$_5$, R$_6$, R$_7$, and R$_8$ are independently selected from the group consisting of hydrogen, alkyl, cycloalkyl, aromatic, and heteroaromatic; R$_2$ and R$_3$ are each independently selected from the group consisting of hydrogen, alkyl, cycloalkyl, aromatic, and heteroaromatic; NH—R$_4$ is peptidyl or R$_4$ is independently selected from the group consisting of hydrogen, alkyl, cycloalkyl, aromatic, and heteroaromatic; R$_5$ is selected from the group consisting of hydrogen, alkyl, cycloalkyl, aromatic, and heteroaromatic; andnon-hydrogen R$_1$, R$_2$, R$_3$, R$_4$, and R$_5$ can independently be substituted with alkylamino, alkoxy, amino, halide, nitro, sulfate, sulfonamide, sulfoxide, or thiol ether.

Preferred embodiments specifically exclude compounds previously disclosed in Getman DP et al., *J Med Chem* 36:288–291 (1993). Thus, preferred embodiments according to this aspect of the instant invention exclude compounds having Formula I, in which (using the convention of Formula I above) R$_2$ is benzyl and R$_1$ is —CO—CH(NHR)CH$_2$CONH$_2$, wherein:

R is carbobenzyloxy, R$_3$ is methyl, and R$_4$ is methyl;

R is carbobenzyloxy, R$_3$ is methyl, and R$_4$ is n-butyl;

R is carbobenzyloxy, R$_3$ is isobutyl, and R$_4$ is methyl;

R is carbobenzyloxy, R$_3$ is isobutyl, and R$_4$ is n-butyl;

R is quinolinyl-2-carboxamide, R$_3$ is isobutyl, and R$_4$ is n-butyl;

R is carbobenzyloxy, R$_3$ is isobutyl, and R$_4$ is n-propyl;

R is carbobenzyloxy, R$_3$ is isobutyl, and R$_4$ is ethyl;

R is carbobenzyloxy, R$_3$ is isobutyl, and R$_4$ is isopropyl;

R is carbobenzyloxy, R$_3$ is isobutyl, and R$_4$ is tert-butyl;

R is quinolinyl-2-carboxamide, R$_3$ is isobutyl, and R$_4$ is tert-butyl;

R is carbobenzyloxy, R$_3$ is isopentyl, and R$_4$ is tert-butyl;

R is quinolinyl-2-carboxamide, R$_3$ is isopentyl, and R$_4$ is tert-butyl;

R is carbobenzyloxy, R$_3$ is CH$_2$C$_6$H$_{11}$, and R$_4$ is tert-butyl;

R is quinolinyl-2-carboxamide, R$_3$ is CH$_2$C$_6$H$_{11}$, and R$_4$ is tert-butyl;

R is carbobenzyloxy, R$_3$ is benzyl, and R$_4$ is tert-butyl;

R is quinolinyl-2-carboxamide, R$_3$ is benzyl, and R$_4$ is tert-butyl;

R is carbobenzyloxy, R$_3$ is (R)—CH(CH$_3$)-phenyl, and R$_4$ is tert-butyl;

R is carbobenzyloxy, R$_3$ is (S)—CH(CH$_3$)-phenyl, and R$_4$ is tert-butyl;

R is carbobenzyloxy, R$_3$ is CH$_2$(4-pyridyl), and R$_4$ is tert-butyl; or

R is quinolinyl-2-carboxamide, R$_3$ is CH$_2$(4-pyridyl), and R$_4$ is tert-butyl.

Preferred embodiments also specifically exclude compounds SC-52151 and SC-55389A previously disclosed in Bryant M et al., *Antimicrob Agents Chemother* 39:2229–2234 (1995) and Smidt M L et al., *Antimicrob Agents Chemother* 41:515–522 (1997). Thus, preferred embodiments according to this aspect of the instant invention exclude compounds having Formula I, in which (using the convention of Formula I above) R$_1$ is —CO—CH(C(CH$_3$)$_3$)NHR wherein R is COCH$_2$NHCH$_3$ HCl, R$_2$ is benzyl, R$_3$ is isopentyl, and R$_4$ is tert-butyl.

Preferred embodiments also specifically exclude compounds disclosed in U.S. Pat. No. 5,457,013 (issued to Talley et al.). Thus, preferred embodiments according to this aspect of the invention exclude compounds having Formula I in which R$_1$ is a radical represented by any of the formulas A1, A2, A3 below:

A1

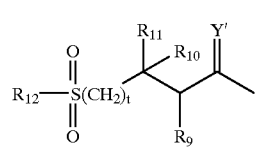

-continued

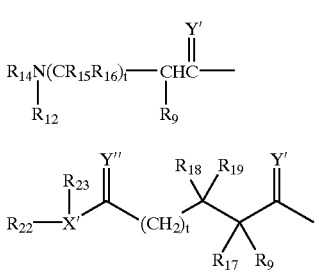

A2

A3 wherein:
R$_{14}$ represents hydrogen and alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxyalkanoyl, heterocyclylcarbonyl, heterocyclyloxycarbonyl, heterocyclylalkanoyl, heterocyclylalkoxycarbonyl, heteroaralkoxycarbonyl, heteroaryloxycarbonyl, heteroaralkanoyl, heteroaroyl, alkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heteroalkyl and heterocycloalkylalkyl radicals or in the case of a disubstituted aminoalkanoyl radical, said substitutents along with the nitrogen atom to which they are attached form a heterocycloalkyl or heteroaryl radical;

R$_{12}$ represents hydrogen and radicals as defined for R$_{13}$ or R$_{14}$ and R$_{12}$ together with the nitrogen to which they are attached form a heterocycloalkyl or heteroaryl radical or when R$_1$ is A1, R$_{12}$ represents hydrogen, radicals as defined for R$_{13}$ and aralkoxycarbonylalkyl and aminocarbonylalkyl and aminoalkyl radicals wherein said amino group may be mono- or disubstituted with substituents selected from alkyl, aryl, aralkyl, cycloalkyl, cycloalkylalkyl, heteroaryl, heteroaralkyl, heteroalkyl, and heterocycloalkylalkyl radicals;

t represents either 0 or 1;

R$_9$ represents hydrogen, —CH$_2$SO$_2$NH$_2$, —CO$_2$CH$_3$, —CH$_2$CO$_2$CH$_3$, —CONH$_2$, —CH$_2$C(O)NHCH$_3$, —CH$_2$C(O)N(CH$_3$)$_2$, —CONHCH$_3$, —CONH(CH$_3$)$_2$, —C(CH$_3$)$_2$(SCH$_3$), —C(CH$_3$)$_2$(S[O]CH$_3$), —C(CH$_3$)$_2$(S[O]$_2$CH$_3$), alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, alloisoleucine, tert-leucine, phenylalanine, ornithine, alanine, histidine, norleucine, glutamine, valine, threonine, serine, aspartic acid, beta-cyano alanine, and allo-threonine side chains;

R$_{15}$ and R$_{16}$ independently represent hydrogen and radicals as defined for R$_9$, or one of R$_{15}$ and R$_{16}$, together with R$_9$ and the carbon atoms to which they are attached, represent a cycloalkyl radical;

R$_{13}$ represents alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals where said substitutents are selected from alkyl, aryl, aralkyl, cycloalkyl, cycloalkylalkyl, heteroaryl, heteroalkyl, heterocycloalkyl, and heterocycloalkylalkyl radicals or, in the case of a disubstituted aminoalkanoyl radical, said substituents along with the nitrogen atom to which they are attached, form a heterocycloalkyl or a heteroaryl radical;

X' represents O C(R$_{21}$) where R$_{21}$ represents hydrogen and alkyl radicals and N;

Y' and Y" independently represent O, S and NR$_{20}$ wherein R$_{20}$ represents hydrogen and radicals as defined for R$_{13}$;

R$_{10}$, R$_{11}$, R$_{17}$, R$_{18}$ and R$_{19}$ represent radicals as defined for R$_9$, or one of R$_9$ and R$_{17}$ together with one of R$_{18}$ and R$_{19}$ and the carbon atoms to which they are attached form a cycloalkyl radical; and R$_{22}$ and R$_{23}$ independently represent hydrogen and radicals as defined for R$_{13}$, or R$_{22}$ and R$_{23}$ together with X' represent cycloalkyl, aryl, heterocyclyl and heteroaryl radicals, provided that when X' is O, R$_{23}$ is absent.

In these and other preferred embodiments R$_2$ is bulky and is selected from the group consisting of cyclohexyl, benzyl and other amino acid side chains. In a more preferred embodiment R$_2$ is benzyl, i.e., the side chain of phenylalanine.

In these and other preferred embodiments R$_3$ is selected from the group consisting of methyl, isopropyl, isobutyl, benzyl and other amino acid side chains. In a more preferred embodiment R$_3$ is benzyl, i.e., the side chain of phenylalanine. Also in these and other preferred embodiments R$_3$ is selected from the group consisting of the side chains of alanine, leucine, and valine.

In these and other preferred embodiments NH—R$_4$ is selected from the group consisting of alanine-phenylalanine O-methyl ester, leucine-alanine O-methyl ester, leucine—leucine O-methyl ester, leucine-phenylalanine O-methyl ester, leucine-valine O-methyl ester, and valine-phenylalanine O-methyl ester. In some preferred embodiments NH—R$_4$ is selected from the group consisting of leucine-valine-alanine O-methyl ester, leucine-valine-leucine O-methyl ester, leucine-valine-phenylalanine O-methyl ester, and leucine-valine—valine O-methyl ester.

In one particularly preferred embodiment R$_1$ is t-butyloxycarbonyl; R$_2$ is benzyl; R$_3$ is benzyl; and NH—R$_4$ is leucine—leucine O-methyl ester.

In another particularly preferred embodiment R$_1$ is t-butyloxycarbonyl; R$_2$ is benzyl; R$_3$ is isobutyl; and NH—R$_4$ is leucine—leucine O-methyl ester.

In another particularly preferred embodiment R$_1$ is t-butyloxycarbonyl; R$_2$ is benzyl; R$_3$ is benzyl; and NH—R$_4$ is alanine-phenylalanine O-methyl ester.

In another particularly preferred embodiment R$_1$ is t-butyloxycarbonyl; R$_2$ is benzyl; R$_3$ is benzyl; and NH—R$_4$ is leucine-valine O-methyl ester.

In another particularly preferred embodiment R$_1$ is t-butyloxycarbonyl; R$_2$ is benzyl; R$_3$ is benzyl; and NH—R$_4$ is valine-phenylalanine O-methyl ester.

In another particularly preferred embodiment R$_1$ is t-butyloxycarbonyl; R$_2$ is benzyl; R$_3$ is benzyl; and NH—R$_4$ is leucine-valine-phenylalanine O-methyl ester.

According to this aspect of the invention, certain embodiments embrace a stereoisomer of the compound of Formula I. Other related embodiments embrace a mixture of different stereoisomers of the compound of Formula I. In certain preferred embodiments all stereocenters are R.

Yet another embodiment is a pharmaceutically acceptable salt of the compound of Formula I.

Also provided is a pharmaceutical composition comprising a compound of Formula I and further comprising a pharmaceutically acceptable carrier. Preferably the pharmaceutically acceptable carrier is adapted for oral administration of a compound of Formula I to a subject. More preferably the pharmaceutically acceptable carrier is adapted for promoting delivery of a compound of Formula I to a brain of a subject.

The invention according to this aspect also provides a method for making a pharmaceutical composition. The method comprises placing a compound of Formula I according to this aspect of the invention in a pharmaceutically acceptable carrier. The method specifically embraces placing the above-identified preferred embodiments of the compound of Formula I in a pharmaceutically acceptable carrier.

In a third aspect the invention provides a method for treating a subject having or at risk of having a β-amyloid-associated disease. The method according to this aspect of the invention involves administering to a subject having or at risk of having a β-amyloid-associated disease a therapeutically effective amount of a compound of Formula I according to the first aspect or second aspect of the invention as described above.

A compound of Formula I as used throughout this application shall refer to a compound of Formula I according to the first aspect of the invention as described above or to a compound of Formula I according to the second aspect of the invention as described above. These two aspects differ primarily from one another in the nature of the $R_1$ group. Compounds of a first aspect of the invention have an $R_1$ group which is not bonded to the Formula I nitrogen via a group

wherein Z is C and X is O, S, or N. Compounds of a second aspect of the invention have an $R_1$ group that can be bonded to the Formula I nitrogen via a group

wherein Z is C and X is O, S, or N.

In a preferred embodiment the β-amyloid-associated disease is a neurodegenerative disease. In a more preferred embodiment the β-amyloid-associated disease is Alzheimer's disease.

In certain embodiments the subject is free of symptoms otherwise calling for treatment with a compound of Formula I. Preferably the subject is free of symptoms of retrovirus infection. More preferably the subject is free of symptoms of human immunodeficiency virus (HIV) infection.

According to this aspect of the invention the compound of Formula I is as described above, including preferred embodiments. The compound of Formula I can be packaged in unit dose form for convenience in dosing.

Preferably the compound of Formula I is administered orally.

In some preferred embodiments $R_1$ is t-butyloxycarbonyl.

In these and other preferred embodiments $R_2$ is bulky and is selected from the group consisting of cyclohexyl, benzyl and other amino acid side chains. In a more preferred embodiment $R_2$ is benzyl, i.e., the side chain of phenylalanine.

In these and other preferred embodiments $R_3$ is selected from the group consisting of methyl, isopropyl, isobutyl, benzyl and other amino acid side chains. In a more preferred embodiment $R_3$ is benzyl, i.e., the side chain of phenylalanine. Also in these and other preferred embodiments $R_3$ is selected from the group consisting of the side chains of alanine, leucine, and valine.

In these and other preferred embodiments NH—$R_4$ is selected from the group consisting of alanine-phenylalanine O-methyl ester, leucine-alanine O-methyl ester, leucine—leucine O-methyl ester, leucine-phenylalanine O-methyl ester, leucine-valine O-methyl ester, and valine-phenylalanine O-methyl ester. In some preferred embodiments NH—$R_4$ is selected from the group consisting of leucine-valine-alanine O-methyl ester, leucine-valine-leucine O-methyl ester, leucine-valine-phenylalanine O-methyl ester, and leucine-valine—valine O-methyl ester.

In one particularly preferred embodiment $R_1$ is t-butyloxycarbonyl; $R_2$ is benzyl; $R_3$ is benzyl; and NH—$R_4$ is leucine—leucine O-methyl ester.

In another particularly preferred embodiment $R_1$ is t-butyloxycarbonyl; $R_2$ is benzyl; $R_3$ is isobutyl; and NH—$R_4$ is leucine—leucine O-methyl ester.

In another particularly preferred embodiment $R_1$ is t-butyloxycarbonyl; $R_2$ is benzyl; $R_3$ is benzyl; and NH—$R_4$ is alanine-phenylalanine O-methyl ester.

In another particularly preferred embodiment $R_1$ is t-butyloxycarbonyl; $R_2$ is benzyl; $R_3$ is benzyl; and NH—$R_4$ is leucine-valine O-methyl ester.

In another particularly preferred embodiment $R_1$ is t-butyloxycarbonyl; $R_2$ is benzyl; $R_3$ is benzyl; and NH—$R_4$ is valine-phenylalanine O-methyl ester.

In another particularly preferred embodiment $R_1$ is t-butyloxycarbonyl; $R_2$ is benzyl; $R_3$ is benzyl; and NH—$R_4$ is leucine-valine-phenylalanine O-methyl ester.

According to this aspect of the invention, certain embodiments embrace a stereoisomer of the compound of Formula I. Other related embodiments embrace a mixture of different stereoisomers of the compound of Formula I. In certain preferred embodiments all stereocenters are R.

According to one embodiment of this aspect of the invention, a compound of Formula I is administered to the subject in combination with an effective amount of another agent useful in the treatment of β-amyloid-associated disease. The method thus embraces the administration of a compound of Formula I in combination with an acetylcholinesterase inhibitor. In other embodiments a compound of Formula I is administered in combination with a compound of Formula II Formula II

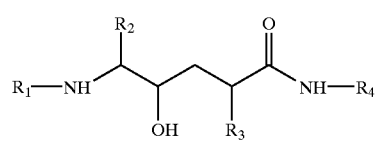

wherein $R_1$ is selected from the group consisting of hydrogen, alkyl, cycloalkyl, aromatic, heteroaromatic, acyl ($R_5C$=O), $R_6O(C$=O), and $R_7R_8N(C$=O), wherein $R_5$, $R_6$, $R_7$, and $R_8$ are independently selected from the group consisting of hydrogen, alkyl, cycloalkyl, aromatic, and heteroaromatic; $R_2$ and $R_3$ are each independently selected from the group consisting of hydrogen, alkyl, cycloalkyl, aromatic, and heteroaromatic; NH—$R_4$ is peptidyl or $R_4$ is independently selected from the group consisting of hydrogen, alkyl, cycloalkyl, aromatic, and heteroaromatic;

and non-hydrogen $R_1$, $R_2$, $R_3$, $R_4$, $R_5$, $R_6$, $R_7$, and $R_8$ can independently be substituted with alkylamino, alkoxy, amino, halide, nitro, sulfate, sulfonamide, sulfoxide, or thiol ether.

In a fourth aspect the invention provides a method for inhibiting activity of an aspartyl protease. The method involves contacting an aspartyl protease, under conditions in which aspartyl protease is enzymatically active, with a compound of Formula I according to the first aspect or the second aspect of the invention as described above.

In certain preferred embodiments the aspartyl protease is not a retroviral protease. Preferably the aspartyl protease is not HIV protease.

In certain preferred embodiments the aspartyl protease is not renin.

In a preferred embodiment the aspartyl protease is a γ-secretase.

In another preferred embodiment the aspartyl protease is a β-secretase.

In a more preferred embodiment the contacting results in a decrease in the generation of amyloid-β peptide.

In certain embodiments the method according to this aspect of the invention is performed in vitro. In certain embodiments the method according to this aspect of the invention is performed in vivo.

In a fifth aspect the invention provides a method for treating a subject having or at risk of having a β-amyloid-associated disease. The method involves administering to a subject having or at risk of having a β-amyloid-associated disease and free of symptoms otherwise calling for treatment with a compound of Formula IA or Formula IB, a therapeutically effective amount of a compound of Formula IA or Formula IB

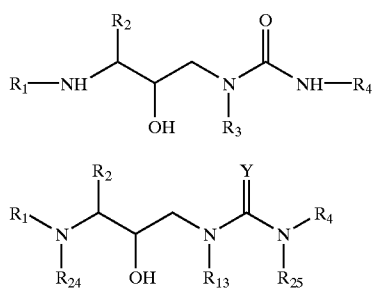

Formula IA

Formula IB wherein, with respect to Formula IA:
(i) $R_2$ is benzyl and $R_1$ is —CO—CH(NHR)CH$_2$CONH$_2$, wherein:
R is carbobenzyloxy, $R_3$ is methyl, and $R_4$ is methyl;
R is carbobenzyloxy, $R_3$ is methyl, and $R_4$ is n-butyl;
R is carbobenzyloxy, $R_3$ is isobutyl, and $R_4$ is methyl;
R is carbobenzyloxy, $R_3$ is isobutyl, and $R_4$ is n-butyl;
R is quinolinyl-2-carboxamide, $R_3$ is isobutyl, and $R_4$ is n-butyl;
R is carbobenzyloxy, $R_3$ is isobutyl, and $R_4$ is n-propyl;
R is carbobenzyloxy, $R_3$ is isobutyl, and $R_4$ is ethyl;
R is carbobenzyloxy, $R_3$ is isobutyl, and $R_4$ is isopropyl;
R is carbobenzyloxy, $R_3$ is isobutyl, and $R_4$ is tert-butyl;
R is quinolinyl-2-carboxamide, $R_3$ is isobutyl, and $R_4$ is tert-butyl;
R is carbobenzyloxy, $R_3$ is isopentyl, and $R_4$ is tert-butyl;
R is quinolinyl-2-carboxamide, $R_3$ is isopentyl, and $R_4$ is tert-butyl;
R is carbobenzyloxy, $R_3$ is CH$_2$C$_6$H$_{11}$, and $R_4$ is tert-butyl;
R is quinolinyl-2-carboxamide, $R_3$ is CH$_2$C$_6$H$_{11}$, and $R_4$ is tert-butyl;
R is carbobenzyloxy, $R_3$ is benzyl, and $R_4$ is tert-butyl;
R is quinolinyl-2-carboxamide, $R_3$ is benzyl, and $R_4$ is tert-butyl;
R is carbobenzyloxy, $R_3$ is (R)—CH(CH$_3$)-phenyl, and $R_4$ is tert-butyl;
R is carbobenzyloxy, $R_3$ is (S)—CH(CH$_3$)-phenyl, and $R_4$ is tert-butyl;
R is carbobenzyloxy, $R_3$ is CH$_2$(4-pyridyl), and $R_4$ is tert-butyl; or
R is quinolinyl-2-carboxamide, $R_3$ is CH$_2$(4-pyridyl), and $R_4$ is tert-butyl; or
(ii) $R_1$ is —CO—CH(C(CH$_3$)$_3$)NHR, wherein: R is COCH$_2$NHCH$_3$ HCl, $R_2$ is benzyl, $R_3$ is isopentyl, and $R_4$ is tert-butyl; and, with respect to Formula IB, $R_1$ is a radical represented by any of the formulas A1, A2, A3 below:

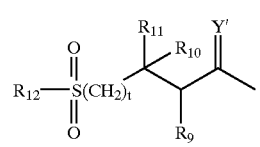

A1

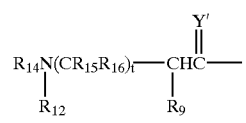

A2

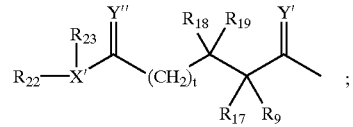

A3

$R_2$ represents alkyl, aryl, cycloalkyl, cycloalkylalkyl and aralkyl radicals, which radicals are optionally substituted with a group selected from —NO$_2$, —OR$_{30}$, —SR$_{30}$, and halogen radicals, wherein $R_{30}$ represents hydrogen and alkyl radicals;

$R_4$ represents radicals represented by the formula:

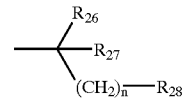

wherein n represents an integer of from 0 to 6, $R_{26}$ and $R_{27}$ independently represent radicals as defined for $R_{13}$ and amino acid side chains selected from the group consisting of valine, isoleucine, glycine, alanine, allo-isoleucine, asparagine, leucine, glutamine, and t-butylglycine or $R_{26}$ and $R_{27}$ together with the carbon atom to which they are attached form a cycloalkyl radical; and $R_{28}$ represents cyano, hydroxyl, alkyl, alkoxy, cycloalkyl, aryl, aralkyl, heterocycloalkyl and heteroaryl radicals and radicals represented by the formulas C(O)R$_{29}$, CO$_2$R$_{29}$, SO$_2$R$_{29}$, SR$_{29}$, CONR$_{29}$R$_{21}$, OR$_{29}$, CF$_3$ and NR$_{29}$R$_{21}$ wherein $R_{29}$ and $R_{21}$ independently represent hydrogen and radicals as defined for $R_{13}$ or $R_{29}$ and $R_{21}$ together with a nitrogen to which they are attached in the formula —NR$_{29}$R$_{21}$ represent heterocycloalkyl and heteroaryl radicals;

$R_{24}$ represents hydrogen and alkyl radicals;

$R_{25}$ independently represents hydrogen and radicals as defined by $R_{13}$; and $R_{13}$ represents alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals where said substitutents are selected from alkyl, aryl, aralkyl, cycloalkyl, cycloalkylalkyl, heteroaryl, heteroalkyl, heterocycloalkyl, and heterocycloalkylalkyl radicals or, in the case of a disubstituted aminoalkanoyl radical, said substituents along with the nitrogen atom to which they are attached, form a heterocycloalkyl or a heteroaryl radical; wherein:

$R_{14}$ represents hydrogen and alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxyalkanoyl, heterocyclylcarbonyl, heterocyclyloxycarbonyl, heterocyclylalkanoyl, heterocyclylalkoxycarbonyl, heteroaralkoxycarbonyl, heteroaryloxycarbonyl, heteroaralkanoyl, heteroaroyl, alkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heteroalkyl and heterocycloalkylalkyl radicals or in the case of a disubstituted aminoalkanoyl radical, said substitutents along with the nitrogen atom to which they are attached form a heterocycloalkyl or heteroaryl radical;

$R_{12}$ represents hydrogen and radicals as defined for $R_{13}$ or $R_{14}$ and $R_{12}$ together with the nitrogen to which they are attached form a heterocycloalkyl or heteroaryl radical or when $R_1$ is A1, $R_{12}$ represents hydrogen, radicals as defined for $R_{13}$ and aralkoxycarbonylalkyl and aminocarbonylalkyl and aminoalkyl radicals wherein said amino group may be mono- or disubstituted with substituents selected from alkyl, aryl, aralkyl, cycloalkyl, cycloalkylalkyl, heteroaryl, heteroaralkyl, heteroalkyl, and heterocycloalkylalkyl radicals;

t represents either 0 or 1;

$R_9$ represents hydrogen, —$CH_2SO_2NH_2$, —$CO_2CH_3$, —$CH_2CO_2CH_3$, —$CONH_2$, —$CH_2C(O)NHCH_3$, —$CH_2C(O)N(CH_3)_2$, —$CONHCH_3$, —$CONH(CH_3)_2$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, alloisoleucine, tert-leucine, phenylalanine, omithine, alanine, histidine, norleucine, glutamine, valine, threonine, serine, aspartic acid, beta-cyano alanine, and allo-threonine side chains;

$R_{15}$ and $R_{16}$ independently represent hydrogen and radicals as defined for $R_9$, or one of $R_{15}$ and $R_{16}$, together with $R_9$ and the carbon atoms to which they are attached, represent a cycloalkyl radical;

X' represents O, $C(R_{21})$ where $R_{21}$ represents hydrogen and alkyl radicals and N;

Y, Y' and Y" independently represent O, S and $NR_{20}$ wherein $R_{20}$ represents hydrogen and radicals as defined for $R_{13}$;

$R_{10}$, $R_{11}$, $R_{17}$, $R_{18}$ and $R_{19}$ represent radicals as defined for $R_9$, or one of $R_9$ and $R_{17}$ together with one of $R_{18}$ and $R_{19}$ and the carbon atoms to which they are attached form a cycloalkyl radical; and $R_{22}$ and $R_{23}$ independently represent hydrogen and radicals as defined for $R_{13}$, or $R_{22}$ and $R_{23}$ together with X' represent cycloalkyl, aryl, heterocyclyl and heteroaryl radicals, provided that when X' is O, $R_{23}$ is absent, whereby the β-amyloid disease is treated.

BRIEF DESCRIPTION OF THE DRAWINGS

The following figures are provided for illustrative purposes only and are not required for understanding or practicing the invention.

DETAILED DESCRIPTION

I. Definitions

Figure 1:
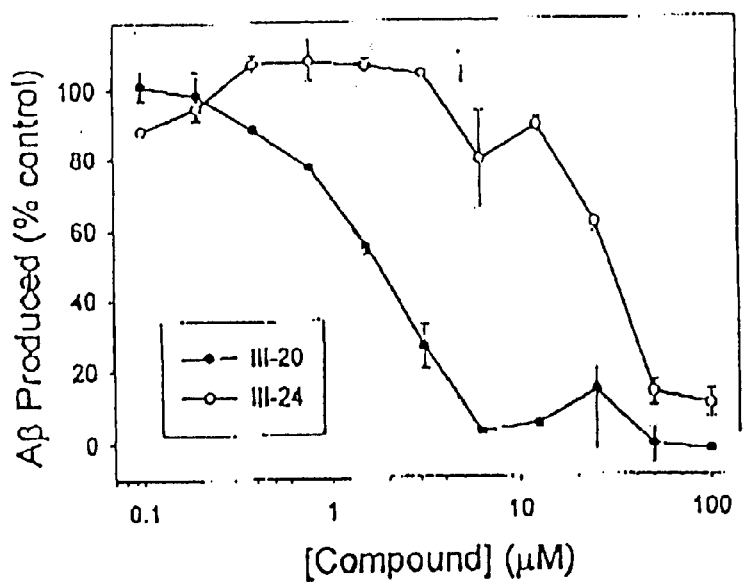
FIG. 1 is a graph that depicts the inhibitory effect of compounds III-20 (filled circles) and III-24 (open circles) on the production of Aβ peptide as measured by enzyme-linked immunosorbent assay (ELISA).

Alkyl groups can be linear or branched, saturated or unsaturated, and have up to about ten carbon atoms. One or more hydrogen atoms can also be replaced by a substituent group selected from acyl, amino, carboalkoxy, carboxy, carboxyamido, cyano, halo, hydroxy, nitro, thio, alkyl, cycloalkyl, alkoxy, aryloxy, sulfoxy, and guanido groups. Preferred alkyl groups are "lower alkyl" groups having one to about four carbon atoms. Equally preferred alkyl groups are unsubstituted or include amino, carboxy, carboxyamido, hydroxy, thio and guanido groups. More preferred alkyl groups are methyl, isopropyl, isobutyl, 1-methylpropyl, thiomethylethyl, hydroxymethyl, 1-hydroxyethyl, thiomethyl, carboxyamidomethyl, carboxyamidoethyl, carboxymethyl, carboxyethyl, aminobutyl and guanido.

Cycloalkyl groups have, preferably, saturated or partially unsaturated ring systems, each containing zero to four hetero atoms selected from oxygen, nitrogen and sulfur in a single or fused carbocyclic or heterocyclic ring system having from three to fifteen ring members. Cycloalkyl groups include multicyclic groups having two, three, or more saturated or partially unsaturated rings that can be single, fused, or a combination of single and fused rings. One or more hydrogen atoms may also be replaced by a substituent group selected from acyl, amino, carboalkoxy, carboxy, carboxyamido, cyano, halo, hydroxy, nitro, oxo, thio, alkyl, aryl, cycloalkyl, alkoxy, aryloxy, and guanido groups or two substituents together may form a fused cycloalkyl ring. Examples of a cycloalkyl group include cyclopropyl, cyclobutyl, cyclohexyl, cycloheptyl, morpholinyl, piperidinyl, and pyrrolidinyl. An example of a multicyclic cycloalkyl group is adamantyl. An alkoxy group denotes an oxygen atom substituted with an acyl, alkyl or cycloalkyl group. Examples include methoxy, tert-butyloxy, benzyloxy, and cyclohexyloxy. An aryloxy group denotes an oxygen atom substituted with an aryl group. Examples of aryloxy groups are phenoxy, 4-carbobenzyloxyphenoxy, 4-phenoxyphenoxy. Sulfoxy groups comprise a hexavalent sulfur atom bound to two or three substituents selected from the group consisting of oxo, alkyl, aryl and cycloalkyl groups, wherein at least one of said substituents is oxo.

Aromatic groups can contain a single or fused carbocyclic ring system, having from five to fifteen ring members. One or more hydrogen atoms may also be replaced by a substituent group selected from acyl, amino, carboalkoxy, carboxy, carboxyamido, cyano, halo, hydroxy, nitro, thio, alkyl, aryl, cycloalkyl, alkoxy, aryloxy, sulfoxy, and guanido groups. Arylalkyl groups embrace aryl-substituted alkyl groups. Preferred arylalkyl groups include benzyl, 3-indolylmethyl, 4-hydroxybenzyl, 5-imidazolylmethyl.

Heteroaromatic groups can contain one to four hetero atoms selected from oxygen, nitrogen and sulfur in a single or fused heterocyclic ring system, having from five to fifteen ring members. One or more hydrogen atoms may also be replaced by a substituent group selected from acyl, amino, carboalkoxy, carboxy, carboxyamido, cyano, halo, hydroxy, nitro, thio, alkyl, aryl, cycloalkyl, alkoxy, aryloxy, sulfoxy, and guanido groups. Arylalkyl groups embrace aryl-substituted alkyl groups. Preferred arylalkyl groups include benzyl, 3-indolylmethyl, 4-hydroxybenzyl, 5-imidazolylmethyl.

Peptidyl groups can contain one to ten amino acid residues, amino acid side chains, or amino acid analog residues, usually, but not always, joined in a linear or cyclic fashion by peptide linkages. Amino acid residues can include naturally-occurring and non-naturally-occurring amino acids, examples of which are well known in the art. In certain embodiments amino acid residues or peptidyl groups can be terminated by O-methyl ester linkages. In other embodiments adjacent amino acid residues can be joined together by peptide linkages. In certain preferred embodiments, the peptidyl group includes one to four amino acid residues. In certain more preferred embodiments, a peptidyl group includes two amino acid residues. In certain more preferred embodiments, a peptidyl group includes three amino acid residues. In certain more preferred embodiments, a peptidyl group is selected from the group alanine, leucine, phenylalanine, valine, alanine-phenylalanine, leucine-alanine, leucine—leucine, leucine-phenyalanine, leucine-valine, valine-phenylalanine, leucine-valaine-alanine, leucine-valine-leucine, leucine-valine-phenylalanine, and leucine-valine-valine.

Notwithstanding the definitions above, with respect to preferred embodiments of the novel compounds of Formula I of the instant invention, compounds previously disclosed in Getman D P et al., *J Med Chem* 36:288–291 (1993), related U.S. Pat. Nos. 5,457,013 and 5,698,569 (issued to Talley et al.), and Smidt M L et al., *Antimicrob Agents Chemother* 41:515–522 (1997) are specifically excluded. Thus, preferred embodiments according to the first and second aspects of the invention exclude compounds having Formula I in which (using the convention of Formula I above) $R_2$ is benzyl and $R_1$ is —CO—CH(NHR)CH$_2$CONH$_2$, wherein:

R is carbobenzyloxy, $R_3$ is methyl, and $R_4$ is methyl;
R is carbobenzyloxy, $R_3$ is methyl, and $R_4$ is n-butyl;
R is carbobenzyloxy, $R_3$ is isobutyl, and $R_4$ is methyl;
R is carbobenzyloxy, $R_3$ is isobutyl, and $R_4$ is n-butyl;
R is quinolinyl-2-carboxamide, $R_3$ is isobutyl, and $R_4$ is n-butyl;
R is carbobenzyloxy, $R_3$ is isobutyl, and $R_4$ is n-propyl;
R is carbobenzyloxy, $R_3$ is isobutyl, and $R_4$ is ethyl;
R is carbobenzyloxy, $R_3$ is isobutyl, and $R_4$ is isopropyl;
R is carbobenzyloxy, $R_3$ is isobutyl, and $R_4$ is tert-butyl;
R is quinolinyl-2-carboxamide, $R_3$ is isobutyl, and $R_4$ is tert-butyl (compound SC-52151);
R is carbobenzyloxy, $R_3$ is isopentyl, and $R_4$ is tert-butyl;
R is quinolinyl-2-carboxamide, $R_3$ is isopentyl, and $R_4$ is tert-butyl;
R is carbobenzyloxy, $R_3$ is $CH_2C_6H_{11}$, and $R_4$ is tert-butyl;
R is quinolinyl-2-carboxamide, $R_3$ is $CH_2C_6H_{11}$, and $R_4$ is tert-butyl;
R is carbobenzyloxy, $R_3$ is benzyl, and $R_4$ is tert-butyl;
R is quinolinyl-2-carboxamide, $R_3$ is benzyl, and $R_4$ is tert-butyl;
R is carbobenzyloxy, $R_3$ is (R)—CH(CH$_3$)-phenyl, and $R_4$ is tert-butyl;
R is carbobenzyloxy, $R_3$ is (S)—CH(CH$_3$)-phenyl, and $R_4$ is tert-butyl;
R is carbobenzyloxy, $R_3$ is CH$_2$(4-pyridyl), and $R_4$ is tert-butyl; or
R is quinolinyl-2-carboxamide, $R_3$ is CH$_2$(4-pyridyl), and $R_4$ is tert-butyl.

Preferred embodiments according to the first and second aspects of the invention also specifically exclude compound SC-55389A previously disclosed Smidt M L et al., *Antimicrob Agents Chemother* 41:515–522 (1997), i.e., compounds having Formula I, in which (using the convention of Formula I above) $R_2$ is benzyl and $R_1$ is —CO—CH(C(CH$_3$)$_3$)NHR, wherein R is COCH$_2$NHCH$_3$ HCl, $R_3$ is isopentyl, and $R_4$ is tert-butyl.

Preferred embodiments also specifically exclude compounds disclosed in U.S. Pat. No. 5,457,013 (issued to Talley et al.). Thus, preferred embodiments according to the first and second aspects of the invention exclude compounds having Formula I in which $R_1$ is a radical represented by any of the formulas A1, A2, A3 below:

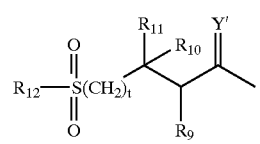

A1

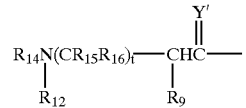

A2

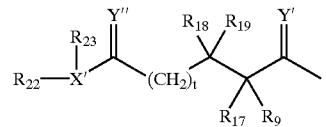

A3 wherein:

$R_{14}$ represents hydrogen and alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxyalkanoyl, heterocyclylcarbonyl, heterocyclyloxycarbonyl, heterocyclylalkanoyl, heterocyclylalkoxycarbonyl, heteroaralkoxycarbonyl, heteroaryloxycarbonyl, heteroaralkanoyl, heteroaroyl, alkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heteroalkyl and heterocycloalkylalkyl radicals or in the case of a disubstituted aminoalkanoyl radical, said substitutents along with the nitrogen atom to which they are attached form a heterocycloalkyl or heteroaryl radical;

$R_{12}$ represents hydrogen and radicals as defined for $R_{13}$ or $R_{14}$ and $R_{12}$ together with the nitrogen to which they are attached form a heterocycloalkyl or heteroaryl radical or when $R_1$ is A1, $R_{12}$ represents hydrogen, radicals as defined for $R_{13}$ and aralkoxycarbonylalkyl and aminocarbonylalkyl and aminoalkyl radicals wherein said amino group may be mono- or disubstituted with substituents selected from alkyl, aryl, aralkyl, cycloalkyl, cycloalkylalkyl, heteroaryl, heteroaralkyl, heteroalkyl, and heterocycloalkylalkyl radicals;

t represents either 0 or 1;

$R_9$ represents hydrogen, —$CH_2SO_2NH_2$, —$CO_2CH_3$, —$CH_2CO_2CH_3$, —$CONH_2$, —$CH_2C(O)NHCH_3$, —$CH_2C(O)N(CH_3)_2$, —$CONHCH_3$, —$CONH(CH_3)_2$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, aspartic acid, beta-cyano alanine, and allo-threonine side chains;

$R_{15}$ and $R_{16}$ independently represent hydrogen and radicals as defined for $R_9$, or one of $R_{15}$ and $R_{16}$, together with $R_9$ and the carbon atoms to which they are attached, represent a cycloalkyl radical;

$R_{13}$ represents alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals where said substitutents are selected from alkyl, aryl, aralkyl, cycloalkyl, cycloalkylalkyl, heteroaryl, heteroalkyl, heterocycloalkyl, and heterocycloalkylalkyl radicals or, in the case of a disubstituted aminoalkanoyl radical, said substituents along with the nitrogen atom to which they are attached, form a heterocycloalkyl or a heteroaryl radical;

X' represents O, $C(R_{21})$ where $R_{21}$ represents hydrogen and alkyl radicals and N;

Y' and Y" independently represent O, S and $NR_{20}$ wherein $R_{20}$ represents hydrogen and radicals as defined for $R_{13}$;

$R_{10}$, $R_{11}$, $R_{17}$, $R_{18}$ and $R_{19}$ represent radicals as defined for $R_9$, or one of $R_9$ and $R_{17}$ together with one of $R_{18}$ and $R_{19}$ and the carbon atoms to which they are attached form a cycloalkyl radical; and $R_{22}$ and $R_{23}$ independently represent hydrogen and radicals as defined for $R_{13}$, or $R_{22}$ and $R_{23}$ together with X' represent cycloalkyl, aryl, heterocyclyl and heteroaryl radicals, provided that when X' is O, $R_{23}$ is absent.

Notwithstanding the foregoing, the invention also embraces the second medical use of the above-noted known compounds in a method for treating a subject having or susceptible to having a β-amyloid-associated disease wherein the subject is free of symptoms otherwise calling for treatment with such compounds, e.g., symptoms of infection with a retrovirus such as HIV.

The pharmaceutically acceptable salts of the compounds of Formula I include acid addition salts and base addition salts. The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of Formula I may be prepared from an inorganic acid or an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically acceptable base addition salts of compounds of Formula I include, but are not limited to, metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine and procaine. All of these salts may be prepared by conventional means from the corresponding compound of Formula I by treating, for example, the compound of Formula I with the appropriate acid or base.

The compounds of Formula I have centers of asymmetry, i.e., chiral centers, including one at the alcohol. The absolute configuration of these centers can be assigned by the stereochemical descriptors R and S, this R and S notation corresponding to the rules described in *Pure Appl Chem* 45:11–30 (1976). Unless otherwise indicated, the chemical designation of compounds as used herein includes all possible stereochemical isomeric forms.

The compounds of Formula I are thus capable of existing in the form of optical isomers as well as in the form of racemic or non-racemic mixtures thereof. The compounds of Formula I can be utilized in the present invention as a single diastereomer or as a mixture of stereochemical isomeric forms. Diastereoisomers can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of Formula I can likewise be obtained by utilizing optically active starting materials. These isomers may be in the form of a free acid, a free base, an ester or a salt.

The invention also embraces isolated compounds. An isolated compound refers to a compound which represents at least 10 percent of the compound present in the mixture and exhibits a detectable (i.e., statistically significant) biological activity when tested in conventional biological assays such as those described herein. Preferably the isolated compound represents at least 50 percent of the mixture; more preferably at least 80 percent of the mixture; and most preferably at least 90 percent or at least 95 percent of the mixture.

The invention embraces compounds and methods useful for inhibiting the enzymatic activity of certain aspartyl proteases. An aspartyl protease refers to an enzyme with an active site characterized by two aspartate residues which are adjacent to one another in three-dimensional space and coordinated by a water molecule, that catalyzes the hydrolysis of its substrate. Aspartyl proteases include cathepsin D, renin, HIV protease, pepsin, and β- and γ-secretase. Vassar R et al., *Science* 286:735–741 (1999); Leung D et al., *J Med Chem* 43:305–341 (2000); Wolfe M S et al., *Biochemistry* 38:4720–4727 (1999).

As mentioned elsewhere herein, in certain embodiments a subject is free of symptoms of retrovirus infection, including in particular infection by human immunodeficiency virus (HIV). Retroviruses are RNA viruses that belong to the family Retroviridae. These viruses characteristically contain an RNA-dependent DNA polymerase (reverse transcriptase) that directs the synthesis of a DNA form of the viral genome after infection of a host cell. The Retroviridae family includes the subfamilies Oncovirinae (oncogenic viruses), for example human T-cell lymphotropic virus (HTLV), Rous sarcoma virus, Abelson leukemia virus, murine mammary tumor virus, and Mason-Pfizer monkey virus; Lentivirinae (slow viruses), which includes HIV-1, HIV-2, Visna virus, and feline immunodeficiency virus; and Spumavirinae (foamy viruses), for example Simian foamy virus and human foamy virus. As their names suggest, many of these viruses cause symptoms related to malignant transformation of infected cells and induction of immunodeficiency that leads to opportunistic infections. Symptoms of infection by specific retroviruses are well known in the art and are described, for example, in *Harrison's Principles of Internal Medicine*, 14<sup>th</sup> Ed., Fauci A S et al., eds, New York: McGraw-Hill, 1998, Chapters 192 and 308. As used herein, symptoms of HIV infection include both clinical symptoms and levels of viremia associated with any stage of HIV disease, including acute HIV syndrome, asymptomatic stage, early symptomatic disease, neurologic disease, secondary infections, neoplasms, and organ-specific syndromes.

II. Description

According to one aspect of the invention, compounds of Formula I are provided. The compounds are useful for inhibiting the enzymatic activity of certain aspartyl proteases. The compounds are particularly potent inhibitors of γ-secretase, the enzyme that catalyzes the final step in the generation of amyloid-β peptide from the amyloid-β precursor protein (APP). The compounds are also believed by the applicants to be particularly potent inhibitors of β-secretase, another enzyme that catalyzes a late step in the generation of amyloid-β peptide from APP.

γ-Secretase catalyzes the final step in the generation of amyloid-β peptide (Aβ) from the amyloid-β precursor protein (APP) and plays a central role in the pathogenesis of Alzheimer's disease (AD). Inhibition of this enzyme by transition-state analogues is consistent with an aspartyl protease mechanism, while substrate modeling and mutagenesis suggest an intramembranous proteolysis. The polytopic presenilins are intimately associated with γ-secretase activity. The requirement for two transmembrane aspartates for both γ-secretase activity and presenilin endoproteolysis into two subunits suggests that presenilin is the catalytic unit of γ-secretase, an intramembrane-cleaving protease that undergoes autoactivation from a holoprotein zymogen.

This aspect of the invention is based, in part, on the discovery that certain transition-state analogue inhibitors, designed to interact with the γ-secretase active site, bind directly to presenilin subunits. Although not wishing to be bound to any particular theory or mechanism, it is believed that the compounds of Formula I function as small peptidomimetics containing a (hydroxyethyl)urea moiety, an aspartyl protease transition-state mimetic that allows incorporation of a P1' substituent. Compounds of this type can be readily synthesized without undue experimentation in a few simple steps from commercially available materials. Significantly, compounds of Formula I can inhibit γ-secretase activity in whole cells at sub-micromolar concentrations. Production of total Aβ and the more fibrillogenic Aβ$_{42}$ is effectively blocked by these compounds, and membrane-associated APP C-terminal fragments (γ-secretase substrates), are elevated in a dose-dependent manner.

A preferred class of compounds of Formula I includes compounds in which $R_1$ is t-butyloxycarbonyl.

In these and other preferred classes of compounds of Formula I, $R_2$ is bulky and is selected from cyclohexyl, benzyl or other amino acid side chains.

In these and yet other preferred classes of compounds of Formula I, $R_3$ is methyl, isopropyl, isobutyl, benzyl or other amino acid side chains.

Any of the compounds shown in Table 1 below are non-limiting, representative examples of this preferred class of compounds. These are characterized by $R_1$ that is t-butyloxycarbonyl, $R_2$ and $R_3$ that are independently selected amino acid side chains, and NH—$R_4$ that is peptidyl O-methyl ester.

In these and other preferred classes of compounds of Formula I includes compounds in which NH—$R_4$ is leucine—leucine O-methyl ester or leucine-phenylalanine O-methyl ester.

In a more preferred class of compounds of Formula I, $R_1$ is t-butyloxycarbonyl; $R_2$ is benzyl; $R_3$ is benzyl; and NH—$R_4$ is leucine—leucine O-methyl ester. This compound has the structural formula

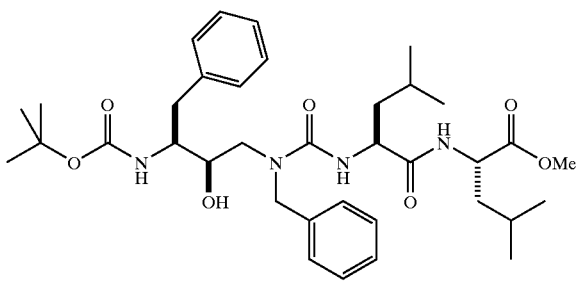

This particular compound is referred to as III-20 in the Examples section below.

In a second more preferred class of compounds of Formula I, $R_1$ is t-butyloxycarbonyl; $R_2$ is benzyl; $R_3$ is isobutyl; and NH—R$_4$ is leucine—leucine O-methyl ester. This compound has the structural formula

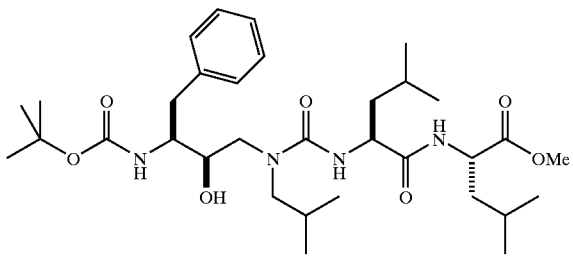

In another preferred class of compounds of Formula I, R$_1$ is t-butyloxycarbonyl; R$_2$ is benzyl, R$_3$ is benzyl, and NH—R$_4$ is alanine-phenylalanine O-methyl ester.

In another preferred class of compounds of Formula I, R$_1$ is t-butyloxycarbonyl; R$_2$ is benzyl, R$_3$ is benzyl, and NH—R$_4$ is leucine-valine O-methyl ester.

In another preferred class of compounds of Formula I, R$_1$ is t-butyloxycarbonyl; R$_2$ is benzyl, R$_3$ is benzyl, and NH—R$_4$ is valine-phenylalanine O-methyl ester.

In yet another preferred class of compounds of Formula I, R$_1$ is t-butyloxycarbonyl; R$_2$ is benzyl, R$_3$ is benzyl, and NH—R$_4$ is leucine-valine-phenylalanine O-methyl ester.

In certain embodiments the compound of Formula I can be a pure R stereoisomer. In alternative embodiments, the compound of Formula I can be a pure S stereoisomer. In yet other alternative embodiments, a compound of Formula I can include a mixture of R and S stereoisomers, wherein the ratio of the contribution of one stereoisomer to the other can range from about 1:99 to about 99:1. In certain preferred embodiments the compound of Formula I is a pure R stereoisomer.

Certain embodiments embrace a salt of a compound of Formula I. In a preferred embodiment, the salt of the compound is a pharmaceutically acceptable salt as defined above.

In yet other embodiments, the composition of the invention is a pharmaceutical composition that includes a compound of Formula I prepared in a pharmaceutically acceptable carrier. The pharmaceutically acceptable carrier can be selected on the basis of the desired route of administration of the compound. For example, in a preferred embodiment the carrier is suitable for oral administration. In a more preferred embodiment, the carrier is suitable for promoting delivery of the compound to the brain. Carriers that can promote delivery of the compound to the brain can include any carrier that promotes translocation across the blood-brain barrier and any carrier that promotes uptake of the compound by neural cells. Examples of such carriers include those disclosed in U.S. Pat. No. 5,604,198 (issued to Poduslo et al.), U.S Pat. No. 5,827,819 (issued to Yatvin et al.), U.S. Pat. No. 5,919,815 (issued to Bradley et al.), U.S. Pat. No. 5,955,459 (issued to Bradley et al.), and 5,977,174 (issued to Bradley et al.).

The compounds of the present invention are active against a variety of β-amyloid-associated diseases including, for example, Alzheimer's disease and the dementia of Down's syndrome. These neurodegenerative disorders occur in association with, and are believed to be caused by deposition of, amyloid-β peptide in neural tissue, i.e., β-amyloid plaques.

In addition to APP, secretases also have as their substrates members of the Notch family of receptors. De Strooper B et al., Nature 398:518–522 (1999). Notch proteins are ligand-activated transmembrane receptors involved in cell-fate selection throughout development. Notch activation results in transcriptional changes in the nucleus through an association with members of the CSL family of DNA-binding proteins (where CSL stands for CBF1, Su(H), Lag-1). It is believed that Notch is cleaved by a protease, enabling the cleaved fragment to enter the nucleus. Signaling by a constitutively active membrane-bound Notch-1 protein requires the proteolytic release of the Notch intracellular domain (NICD), which interacts preferentially with CSL. Schroeter E H et al., Nature 393:382–386 (1998).

Inhibiting γ-secretase may also be useful in the treatment of Notch-related diseases, including cerebral autosomal dominant arteriopathy with subcortical infarcts and leukoencephalopathy (CADASIL). A Notch-related disease refers to a disease caused by abnormal Notch-related proteolysis or signaling. For example, a Notch-related disease can arise from a mutation in a Notch receptor causing inappropriate, constitutive Notch activity. Schroeter E H et al., Nature 393:382–386 (1998). CADASIL, the most common form of familial vascular dementia, appears to be essentially a disorder of the arteries that is linked to single missense mutations in the Notch 3 gene locus on chromosome 19. Ruchoux M M and Maurage C A, J Neuropathol Exp Neurol 56:947–964 (1997); Thomas N J et al., Ann N Y Acad Sci 903:293–8 (2000). Other Notch-related diseases include certain neoplasms including, for example, acute lymphoblastic T-cell leukemia. Selkoe D J, Curr Opin Neurobiol 10:50–7 (2000); Deftos M L and Bevan M J, Curr Opin Immunol 12:166–72 (2000); Jeffries S and Capobianco A J, Mol Cell Biol 20:3928–3941 (2000); Capobianco A J et al., Mol Cell Biol 17:6265–6273 (1997); Zagouras P et al., Proc Natl Acad Sci USA 92:6414–6418 (1995).

Thus the compounds of the present invention are also believed to be useful in the treatment of Notch-related diseases, including CADASIL and certain types of neoplasia, e.g., certain leukemias. According to this aspect, the method of treating a subject having or at risk of having a Notch-related disease comprises involves administering to a subject having or at risk of having a Notch-related disease a therapeutically effective amount of a compound of Formula I.

In accordance with another aspect of the invention, a method is provided wherein the compositions disclosed herein are used for treating a subject afflicted by or susceptible to a β-amyloid-associated disease. The method involves administering to a subject having or at risk of having a β-amyloid-associated disease a therapeutically effective amount of a compound of Formula I according to the first aspect of the invention or to the second aspect of the invention. Preferred subjects of the present invention have only one type of β-amyloid-associated disease. More preferably, subjects of the present invention have Alzheimer's disease and do not have any other β-amyloid-associated disease.

A subject having a β-amyloid-associated disease is a subject with at least one identifiable sign, symptom, or laboratory finding sufficient to make a diagnosis of a β-amyloid-associated disease in accordance with clinical standards known in the art for identifying such disorder. In some instances, the absence of identifiable signs, symptoms, or laboratory findings may be necessary to make a diagnosis. For example, the diagnosis of Alzheimer's disease is most often made as a diagnosis of exclusion based on positive findings in cognitive testing in conjunction with exclusion of other causes. See, for example, Bird TD, In: Harrison's Principles of Internal Medicine, 14$^{th}$ Ed., Fauci A S et al., eds, New York: McGraw-Hill, 1998, Chapters 26 and 367. In some instances it may be possible to make a tissue diagnosis.

A subject at risk of having a β-amyloid-associated disease is a subject with an identifiable risk factor for developing a β-amyloid-associated disease. For example, a subject at risk of having a β-amyloid-associated disease can include a member in a family with familial Alzheimer's disease. Another example of a subject at risk of having a β-amyloid-associated disease is a subject over the age of 40 with Down's syndrome.

According to this aspect of the invention, the novel compositions disclosed herein are placed in a pharmaceutically acceptable carrier and are delivered to a recipient subject (preferably a human) in accordance with known methods of drug delivery. The compounds of the present invention may be administered alone or in combination with at least one other agent known or believed by the applicants to be useful for treating a β-amyloid-associated disease. In general, the methods of the invention for delivering the compositions of Formula I in vivo utilize art-recognized protocols for delivering the agent with the only substantial procedural modification being the substitution of the compounds of Formula I for the drugs in the art-recognized protocols.

Other agents which are known to be useful in the treatment of a β-amyloid-associated disease include acetylcholinesterase inhibitors, particularly tetrahydroaminoacridine (tacrine hydrochloride, COGNEX® (Parke-Davis)).

Other agents which the applicants believe to be useful in the treatment of a β-amyloid-associated disease include structurally related hydroxyethylene isosteres of general structure of Formula II as described above.

Compounds of Formula II have been reported as inhibitors of aspartyl proteases cathespin D (Argarwal N S and Rich D H, *J Med Chem* 29:2519–24 (1986)), renin (Kati W M et al., *Biochemistry* 26:7621–6 (1987)), and HIV protease (Huff J R, *J Med Chem* 34:2305–14 (1991)) and have more recently been reported as inhibitors of beta-amyloid production (U.S. Pat. No. 5,703,129; Li Y M et al., *Proc Natl Acad Sci USA* 97:6138–43 (2000)).

Surprisingly, the effect of replacing nitrogen in (hydroxyethyl)ureas of Formula I with carbon in hydroxyethylene compounds of Formula II is significant. This replacement removes a key amide bond which applicants believe renders compounds of Formula II more susceptible to metabolic degradation. The synthetic methods for making (hydroxyethyl)ureas of Formula I are relatively simple, rapid, versatile and readily capable of scaling up compared with the structurally related hydroxyethylenes of Formula II. Getman D P et al., *J Med Chem* 36:288–291 (1993). While compounds of Formula II have been reported as inhibitors of β-amyloid production, and compounds related to Formula I have been reported as inhibitors of other aspartyl proteases, compounds of Formula I have not previously been recognized as inhibitors of Alzheimer's aspartyl proteases.

The phrase "therapeutically effective amount" means that amount of a compound which prevents the onset of, alleviates the symptoms of, or stops the progression of a disorder or disease being treated. The phrase "therapeutically effective amount" means, with respect to a β-amyloid-associated disease, that amount of a compound of Formula I which prevents the onset of, alleviates the symptoms of, or stops the progression of a β-amyloid-related disorder or disease. In general such symptoms are, at least in part, the result of the accumulation of increased amounts of amyloid-β peptide in vivo. Thus, a "β-amyloid-associated disease" is a condition that is characterized by certain clinical features and which, it is generally believed, is associated with excessive amounts of amyloid-β peptide. "Excessive," with respect to amounts of amyloid-β peptide, refers to an amount amyloid-β peptide which is (1) greater than the amount of amyloid-β peptide that occurs in a normal, healthy subject, and (2) results in an adverse medical condition. The term "treating" is defined as administering, to a subject, a therapeutically effective amount of a compound (e.g., of Formula I) that is sufficient to prevent the onset of, alleviate the symptoms of, or stop the progression of a disorder or disease being treated. The term "subject," as described herein, is defined as a mammal. In a preferred embodiment, a subject is a human.

The pharmaceutical preparations disclosed herein are prepared in accordance with standard procedures and are administered at dosages that are selected to reduce, prevent, or eliminate, or to slow or halt the progression of, the condition being treated (See, e.g., *Remington's Pharmaceutical Sciences*, Mack Publishing Company, Easton, Pa., and *Goodman and Gilman's The Pharmaceutical Basis of Therapeutics*, Pergamon Press, New York, N.Y., the contents of which are incorporated herein by reference, for a general description of the methods for administering various agents for human therapy). The compositions of Formula I can be delivered using controlled or sustained-release delivery systems (e.g., capsules, bioerodable matrices). Exemplary delayed-release delivery systems for drug delivery that would be suitable for administration of the compositions of Formula I are described in U.S. Pat. No. 5,990,092 (issued to Walsh); U.S. Pat. No. 5,039,660 (issued to Leonard); U.S. Pat. No. 4,452,775 (issued to Kent); and 3,854,480 (issued to Zaffaroni).

The pharmaceutically acceptable compositions of the present invention comprise one or more compounds of Formula I in association with one or more nontoxic, pharmaceutically acceptable carriers and/or diluents and/or adjuvants and/or excipients, collectively referred to herein as "carrier" materials, and if desired other active ingredients.

The compounds of the present invention may be administered by any route, preferably in the form of a pharmaceutical composition adapted to such a route, and would be dependent on the condition being treated. The compounds and compositions may, for example, be administered orally, intravascularly, intramuscularly, subcutaneously, intraperitoneally, or topically. The preferred method of administration is oral administration. In one embodiment the method of administration involves direct administration to brain.

For oral administration, the pharmaceutical compositions may be in the form of, for example, a tablet, capsule, suspension or liquid. The pharmaceutical composition is preferably made in the form of a dosage unit containing a therapeutically effective amount of the active ingredient. Examples of such dosage units are tablets and capsules. For therapeutic purposes, the tablets and capsules can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

The pharmaceutical compositions may also be administered parenterally via injection. Formulations for parenteral administration may be in the form of aqueous or non-aqueous isotonic sterile injection solutions or suspensions. These solutions or suspensions may be prepared from sterile powders or granules having one or more of the carriers mentioned for use in the formulations for oral administration. The compounds may be dissolved in polyethylene glycol, propylene glycol, ethanol, corn oil, benzyl alcohol, sodium chloride, and/or various buffers.

For topical use the compounds of the present invention may also be prepared in suitable forms to be applied to the skin, or mucus membranes of the nose and throat, and may take the form of creams, ointments, liquid sprays or inhalants, lozenges, or throat paints. Such topical formulations further can include chemical compounds such as dimethylsulfoxide (DMSO) to facilitate surface penetration of the active ingredient. Suitable carriers for topical administration include oil-in-water or water-in-oil emulsions using mineral oils, petrolatum and the like, as well as gels such as hydrogel. Alternative topical formulations include shampoo preparations, oral pastes and mouthwash.

For application to the eyes or ears, the compounds of the present invention may be presented in liquid or semi-liquid form formulated in hydrophobic or hydrophilic bases as ointments, creams, lotions, paints or powders.

For rectal administration the compounds of the present invention may be administered in the form of suppositories admixed with conventional carriers such as cocoa butter, wax or other glyceride.

Alternatively, the compounds of the present invention may be in powder form for reconstitution at the time of delivery.

The dosage regimen for treating a β-amyloid-associated disease with the compound and/or compositions of this invention is selected in accordance with a variety of factors, including the type, age, weight, sex and medical condition of the patient, the severity of the β-amyloid-associated disease, the route and frequency of administration, and the particular compound employed. In general, dosages are determined in accordance with standard practice for optimizing the correct dosage for treating a β-amyloid-associated disease.

The dosage regimen can be determined, for example, by following the response to the treatment in terms of cognitive studies. Examples of such cognitive studies are well known in the art, and they include the mini-mental status examination. See, for example, Bird T D, In: *Harrison's Principles of Internal Medicine*, 14$^{th}$ Ed., Fauci A S et al., eds, New York: McGraw-Hill, 1998, Chapter 26. In addition, because the compounds of the invention are believed to inhibit the synthesis of β-amyloid in vivo, the dosage regimen can also be determined by measurement of β-amyloid. It should be noted that β-amyloid is released into the blood and the cerebrospinal fluid (CSF), and is not confined to neural tissue. Therefore, the dosage regimen can also be determined by correlating serial measurement of β-amyloid present in blood or in CSF to the dose of the compositions of this invention. Methods of measuring β-amyloid present in blood or in CSF can include, for example, methods based on Aβ-specific ELISA.

The compositions may contain from 0.01% to 99% by weight of the active ingredient, depending on the method of administration.

In a further aspect of the invention, a method is provided for inhibiting activity of an aspartyl protease. The method involves contacting a compound of Formula I of the first aspect of the invention or of the second aspect of the invention with an aspartyl protease under conditions in which the aspartyl protease is enzymatically active upon its substrate when the compound is not present, in an amount effective to result in a detectable inhibition of the activity of the aspartyl protease. Also included in this method is contacting an aspartyl protease with a combination of two or more compounds of Formula I to inhibit the aspartyl protease. In a preferred embodiment of this aspect of the invention, the aspartyl protease is γ-secretase. In another preferred embodiment, the aspartyl protease is β-secretase. The compounds of Formula I can be used alone or in combination with other compounds that inhibit aspartyl protease activity. In certain embodiments a compound of the invention is contacted with an aspartyl protease in vitro. The aspartyl protease can be isolated or cellular for in vitro assays. In certain other embodiments a compound of the invention is contacted with an aspartyl protease in vivo.

In a preferred embodiment the class of compounds of Formula I useful for this aspect of the invention includes compounds in which $R_1$ is t-butyloxycarbonyl.

In another preferred embodiment the class of compounds of Formula I useful for this aspect of the invention includes compounds in which $R_2$ is cyclohexyl, benzyl, or other amino acid side chain.

In yet another preferred embodiment the class of compounds of Formula I useful for this aspect of the invention includes compounds in which $R_3$ is methyl, isopropyl, isobutyl, benzyl or other amino acid side chain.

In a further preferred embodiment the class of compounds of Formula I useful for this aspect of the invention includes compounds in which NH—$R_4$ is leucine—leucine O-methyl ester or leucine-phenylalanine O-methyl ester.

In a more preferred embodiment the class of compounds of Formula I useful for this aspect of the invention includes compounds in which $R_1$ is t-butyloxycarbonyl; $R_2$ is benzyl; $R_3$ is benzyl; and NH—$R_4$ is leucine—leucine O-methyl ester.

In a second more preferred embodiment the class of compounds of Formula I useful for this aspect of the invention includes compounds in which $R_1$ is t-butyloxycarbonyl; $R_2$ is benzyl; $R_3$ is isobutyl; and NH—$R_4$ is leucine—leucine O-methyl ester.

In another preferred embodiment the class of compounds of Formula I useful for this aspect of the invention includes compounds in which $R_1$ is t-butyloxycarbonyl; $R_2$ is benzyl, $R_3$ is benzyl, and NH—$R_4$ is alanine-phenylalanine O-methyl ester.

In yet another preferred embodiment the class of compounds of Formula I useful for this aspect of the invention includes compounds in which $R_1$ is t-butyloxycarbonyl; $R_2$ is benzyl, $R_3$ is benzyl, and NH—$R_4$ is leucine-valine O-methyl ester.

In yet another preferred embodiment the class of compounds of Formula I useful for this aspect of the invention includes compounds in which $R_1$ is t-butyloxycarbonyl; $R_2$ is benzyl, $R_3$ is benzyl, and NH—$R_4$ is valine-phenylalanine O-methyl ester.

In yet another preferred embodiment the class of compounds of Formula I useful for this aspect of the invention includes compounds in which $R_1$ is t-butyloxycarbonyl; $R_2$ is benzyl, $R_3$ is benzyl, and NH—$R_4$ is leucine-valine-phenylalanine O-methyl ester.

The inhibitory effect of a compound of unknown inhibitory activity can be assessed by monitoring aspartyl protease activity according to standard techniques. For example, a γ-secretase enzyme is maintained under conditions suitable for β-amyloid formation, the enzyme is contacted with the compound to be tested, and formation of the β-amyloid is monitored by standard assay, such as by ELISA. More specifically for γ-secretase, since reduced γ-secretase acitivity leads to an increase in γ-secretase substrate, a γ-secretase enzyme is maintained under conditions suitable for β-amyloid formation, the enzyme is contacted with the compound to be tested, and accumulation or concentration of the γ-secretase substrate is monitored by standard assay, such as by Western blotting. A reduction in the enzyme activity measured in the presence of the compound, as compared with the activity in the absence of compound, is indicative of inhibition of γ-secretase activity by the compound. In an effort to insure the integrity of the assay, a parallel assay is conducted in which the inhibitory activity of a compound of Formula I with known inhibitory activity is assessed. Since the compounds of Formula I are known inhibitors of γ-secretase, they serve as positive controls for the assay of compounds of unknown inhibitory activity. The absence of inhibition in an assay using a compound of Formula I is indicative of a problem in the assay itself.

III. Examples

The following examples are illustrative only and are not intended to limit the scope of the invention in any way.

EXAMPLE 1

Synthesis of Compounds of Formula I.

The method of synthesis is similar to methods beginning with epoxides previously described by Getman, Talley, and Vasquez, the entire contents of which are incorporated herein by reference. Getman D P et al., *J Med Chem* 36:288–291 (1993); U.S. Pat. No. 5,475,013 (issued to Talley et al.); U.S. Pat. No. 5,830,897 (issued to Vasquez et al.). The epoxides can be readily obtained from commercial sources, such as Sigma-Aldrich. Epoxides not commercially available can be prepared according to published methods, for example the method described by Luly, the entire contents of which are incorporated herein by reference. Luly J R et al., *J Org Chem* 52:1487–1492 (1987).

The following describes the synthetic scheme depicted below. Selection of particular starting compounds in order to arrive at the desired end product will be evident to those skilled in the art. To 1 equivalent of commercially available epoxide A (100 mM in 2-propanol) is added 20 equivalents of amine RNH$_2$, and the reaction is refluxed for 18 hours. Solvent is then removed under reduced pressure providing the adduct B directly in the case of volatile amines (e.g., Me-NH$_2$, I-Pr-NH$_2$, I-Bu-NH$_2$). With nonvolatile amines (e.g., PhCH$_2$NH$_2$), the concentrated mixture is taken up into ethyl acetate and washed with water, 1N HCl, saturated NaHCO$_3$ solution, and brine. The organic layer is then dried over Na$_2$SO$_4$, filtered, and concentrated in vacuo to provide adduct B. Yields range from 85 to 100%.

To a 100 mM solution of amine C in methylene chloride is added an equal volume of saturated NaHCO$_3$ solution. The mixture is stirred at 0° C. for 10 minutes, whereupon stirring is ceased. 2 equivalents of phosgene (2 M solution in toluene) is quickly added via syringe to the lower (organic) phase, and the mixture is vigorously stirred for 10 minutes. The mixture is poured into a separatory funnel and extracted three times with methylene chloride. The combined organic layers are dried over Na$_2$SO$_4$, filtered, and concentrated in vacuo to provide isocyanate D in quantitative yield.

1.2 equivalents of isocyanate D is added to a 70 mM solution of B in methylene chloride, and the solution is stirred at ambient temperature for 18 hours. The solvent is then removed in vacuo, and the residue is passed through silica gel, eluting with methylene chloride:methanol (96:4), to provide urea E in 88–100% yield.

To obtain compounds where R$_4$ is a dipeptide ester, a 0.13 M solution compound E1 is treated with 1.1 equivalent of lithium hydroxide (0.5 M in water) and stirred at 0° C. for two hours. The mixture is then transferred to a separatory funnel, and the aqueous phase is brought to pH 1–2 with 1 N HCl and extracted three times with methylene chloride. The combined organic layers are dried over Na$_2$SO$_4$, filtered, and concentrated. The residue is then taken up in dimethylformamide (100 mM) and treated with 1.1 equivalents of uronium coupling agent HATU (PerSeptive Biosystems, Cambridge, Mass.), 3 equivalents of N,N-diisopropylethylamine (DIEA), and 1.25 equivalents of amino ester. After stirring 18 hours, the mixture is taken up in ethyl acetate and washed three times with 1 N HCl, three times with saturated NaHCO$_3$ solution, and three times with brine. The organic layer is dried over Na$_2$SO$_4$, filtered, and concentrated. The residue is then passed through silica gel, eluting with methylene chloride:methanol (96:4), to provide urea F1 in 88–97% yield.

Synthetic Scheme to (Hydroxyethyl)urea Inhibitors

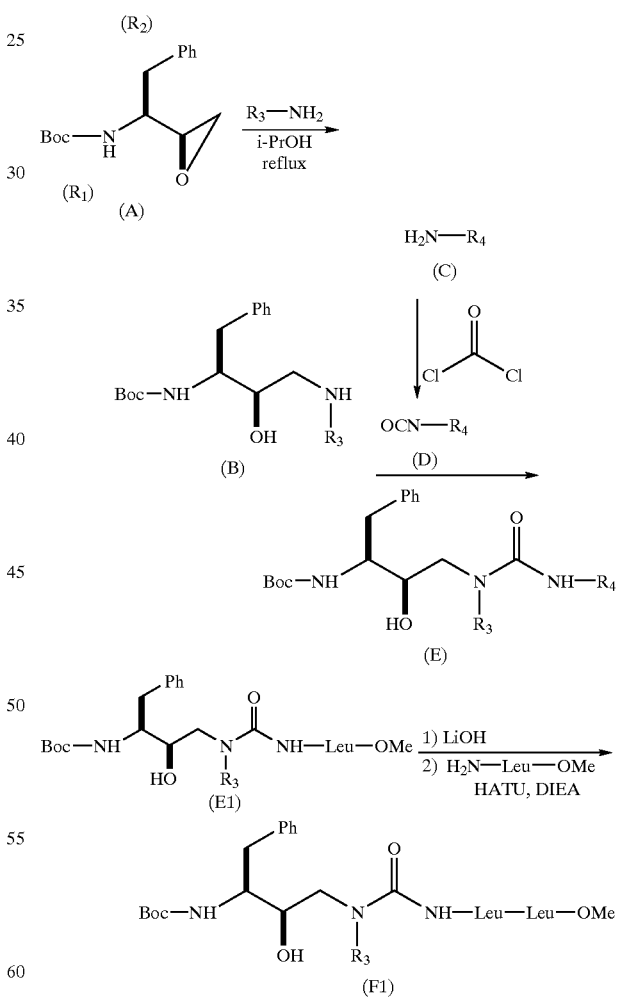

EXAMPLE 2

Inhibition of Aβ Peptide Production in Vitro.

Cell Lines, Compound Treatments, and ELISAs. Cell lines were Chinese hamster ovary (CHO) and SK-N-SH human neuroblastoma cells stably transfected with the 751- or 695-amino acid splicing variants of APP, respectively, and the neo gene, and human embryonic kidney (HEK) 293 cells carrying the same genes (APP695 plus neo) but with the K595N/M596L ("Swedish") double mutation of APP. Xia W et al., *J Biol Chem* 272:7977–7982 (1997); Citron M et al., *Proc Natl Acad Sci USA* 93:13170–13175 (1996). Cells were grown to confluence in Dulbecco's modified Eagle's medium containing 200 μg/ml G418 (Gibco BRL). Stock concentrations of the (hydroxyethyl)urea compounds of the invention in DMSO were added to media to reach the final concentrations with 1% DMSO. Positive controls contained 1% DMSO alone. After 4 hours, the medium was removed and centrifuged at 3000×g for 5 minutes, and the supernatant was stored at −80° C. until the assays were carried out. Sandwich ELISAs for $A\beta_{40}$ and $A\beta_{42}$ were performed as described previously. Johnson-Wood K et al., *Proc Natl Acad Sci USA* 94:1550–1555 (1997); Seubert P et al., *Nature* 359:325–327 (1992). The capture antibodies were 2G3 (to $A\beta_{40}$ residues 33–40) for the $A\beta_{40}$ species and 21F12 (to $A\beta_{42}$ residues 33–42) for the $A\beta_{42}$ species. The reporter antibody was detected using 3,3',5,5'-tetramethylbenzidine (Pierce), measuring at 455 nm for calculating Aβ levels and at 595 nm for normalization.

Compound III-20 (shown above) or compound III-24 (identical to III-20 except $R_4$ is L-phenylalanine O-methyl ester) was added over a range of concentrations (0.1–100 μM) to APP-transfected cells in culture as described. In negative control cultures no compound was added. After 4 hours in culture, supernatants from test and control cultures were assayed by ELISA specific for Aβ peptides, and results were analyzed as percent total or specific Aβ produced compared to control.

As shown in FIG. 1, compound III-20 caused a 50 percent inhibition of total Aβ peptide production at a concentration of about 1 μM. Compound III-24 also inhibited total Aβ peptide production in this assay, however it required a higher concentration, about 50 μM, for 50 percent inhibition.

Figure 2:
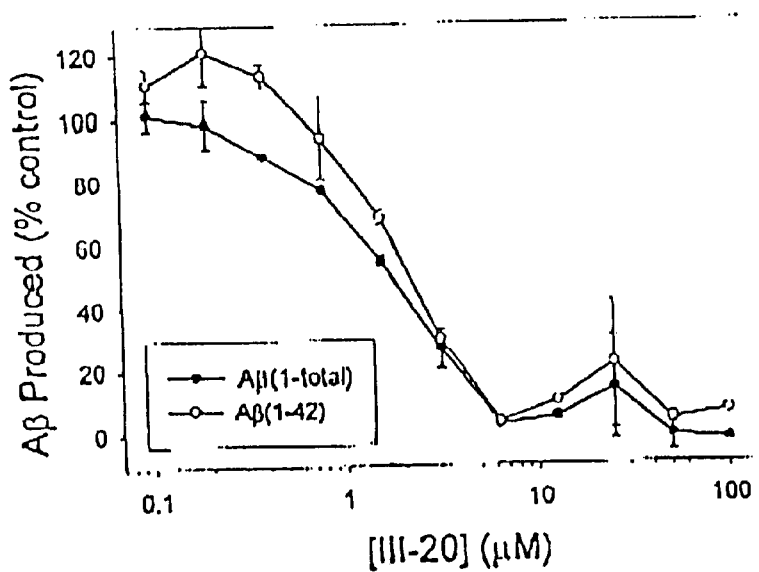
FIG. 2 is a graph that depicts the inhibitory effect of compound III-20 on the production of total Aβ peptide (filled circles) and Aβ$_{1-42}$ (open circles) as measured by ELISA.

As shown in FIG. 2, the inhibitory effect of compound III-20 on the production of $A\beta_{42}$ closely followed the inhibition by compound III-20 of total Aβ production.

EXAMPLE 3

Inhibition of Aβ Peptide Production in Vitro.

A series of related (hydroxyethyl)urea compounds according to Formula I were synthesized and compared in terms of their ability to inhibit Aβ production in APP751-plus neo-transfected CHO cells in vitro. The (hydroxyethyl)urea compounds in this example all had t-butyloxycarbonyl (Boc) as $R_1$, a single amino acid side chain as $R_2$ and as $R_3$, and a dipeptide- or tripeptide-O-methyl ester as $R_4$. The particular compounds can be summarized as shown in Table 1, where amino acids or their side chains are designated using standard one-letter code (A=alanine, F=phenylalanine, L=leucine, V=valine); Boc represents t-butyloxycarbonyl, Ψ represents the core (hydroxyethyl)urea structure, and OMe represents O-methyl ester.

TABLE 1

(Hydroxyethyl)urea compounds for Example 3

| Designation | R1 | R2 | R3 | R4 | IC$_{50}$ (μM) |
|---|---|---|---|---|---|
| FΨALF | Boc | F | A | LF-OMe | 3 |
| FΨFAF | Boc | F | F | AF-OMe | 0.2 |

TABLE 1-continued (Hydroxyethyl)urea compounds for Example 3

| Designation | R1 | R2 | R3 | R4 | IC$_{50}$ (μM) |
|---|---|---|---|---|---|
| FΨFFF | Boc | F | F | FF-OMe | 25 |
| PΨFLA | Boc | F | F | LA-OMe | 2 |
| FΨFLF | Boc | F | F | LF-OMe | 0.5 |
| FΨFLL | Boc | F | F | LL-OMe | 0.5 |
| FΨFLV | Boc | F | F | LV-OMe | 0.2 |
| FΨFVF | Boc | F | F | VF-OMe | 0.2 |
| FΨLLF | Boc | F | L | LF-OMe | 0.5 |
| FΨVLF | Boc | F | V | LF-OMe | 5 |
| FΨFLVA | Boc | F | F | LVA-OMe | 0.8 |
| FΨFLVF | Boc | F | F | LVF-OMe | 0.2 |
| FΨFLVL | Boc | F | F | LVL-OMe | 0.4 |
| FΨFLVV | Boc | F | F | LVV-OMe | 0.8 |

Figure 3:
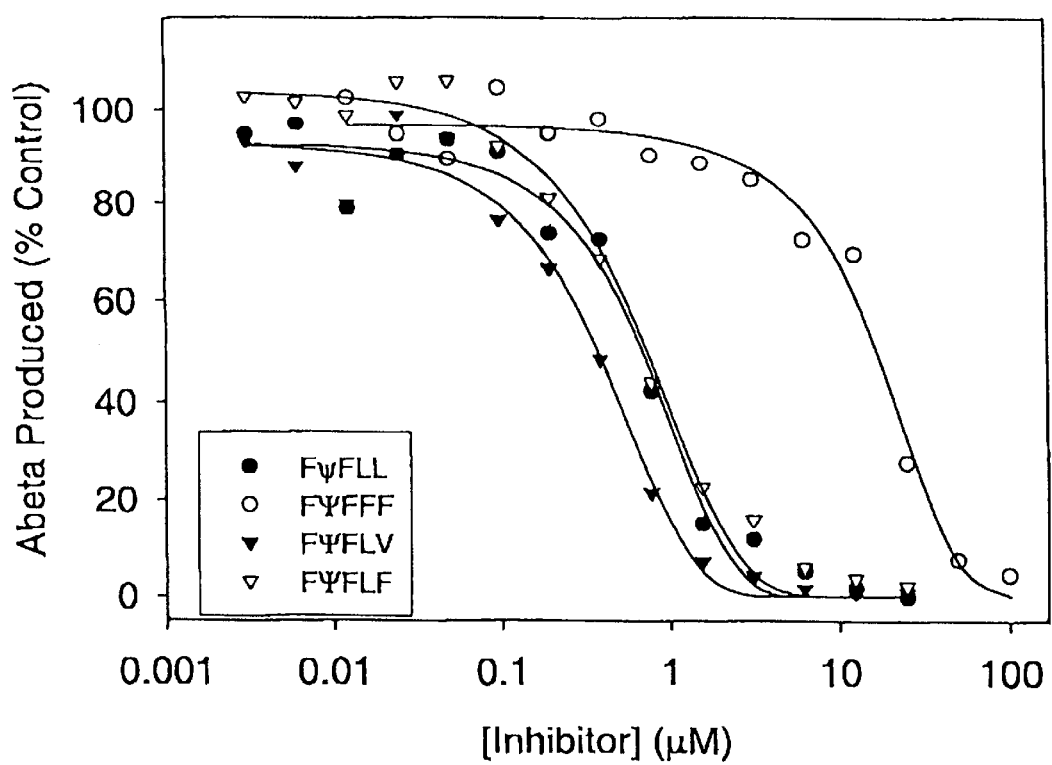
FIG. 3 is a graph that depicts the inhibitory effect of four (hydroxyethyl)urea compounds on the production of total Aβ peptide as measured by ELISA. Open circles, FΨFFF; filled circles, FΨFLL; open triangles, FΨFLF; and filled circles, FΨFLV (see Example 3).

Transfected CHO cells were prepared and maintained as described in Example 2. Stock concentrations of the (hydroxyethyl)urea compounds in Table 1 in DMSO were added to media to attain final concentrations of 0.005 to 100 μM with 1% DMSO. Negative controls contained 1% DMSO alone. After 4 hours, the medium was removed and centrifuged at 3000×g for 5 minutes, and the supernatant was stored at −80° C. until the assays were carried out by ELISA as described for Example 2 above. Results were plotted as percent control Aβ produced versus (hydroxyethyl)urea compound concentration (μM), and (hydroxyethyl)urea compound concentrations at which production was inhibited by 50 percent (IC$_{50}$) were determined. See FIG. 3 and Table 1.

The results demonstrate that for the particular (hydroxyethyl)urea compounds shown in Table 1, IC$_{50}$ values as low as 0.2 μM were attained (FΨFAF, FΨFVF, FΨFLV, and FΨFLVF). All else being equal in this series, it was found that leucine—leucine O-methyl ester, leucine-phenylalanine O-methyl ester, and leucine-valine O-methyl ester were roughly equivalent as $R_4$. Of the (hydroxyethyl)urea compounds tested in this example, the least effective was FΨFFF, in which $R_1$ is Boc, $R_2$ is benzyl (i.e., the side group of phenylalanine), $R_3$ is benzyl (i.e., the side group of phenylalanine), and NH—$R_4$ is phenylalanine—phenylalanine O-methyl ester.

The results also demonstrate that the IC$_{50}$ values were relatively insensitive to the particular amino acid side chains selected for $R_2$ and $R_3$ and for the particular dipeptide and tripeptide O-methyl ester selected for NH—$R_4$. The compositions listed in Table 1 are thus exemplary and are not meant to be limiting with respect to selection of the particular amino acid side chains for $R_2$ and $R_3$ and for the particular dipeptide and tripeptide O-methyl ester for NH—$R_4$.

All of the references, patents and patent publications identified or cited herein are incorporated, in their entirety, by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

We claim:

1. A method of treating a subject having or at risk of having a β-amyloid-associated disease, comprising:
   administering to a subject having or at risk of having Alzheimer disease a therapeutically effective amount of a compound of Formula I

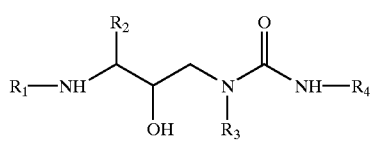
Formula I wherein:

$R_1$ is selected from the group consisting of hydrogen, alkyl, cycloalkyl, aromatic, heteroaromatic, $RO(C=O)$, and $R_7R_8N(C=O)$, wherein $R_6$, $R_7$, and $R_8$ are independently selected from the group consisting of hydrogen, alkyl, cycloalkyl, aromatic, and heteroaromatic, provided R1 is not bonded to the Formula I nitrogen via a group

, wherein Z is C and X is O, S, or N;

$R_2$ and $R_3$ are each independently selected from the group consisting of hydrogen, alkyl, cycloalkyl, aromatic, and heteroaromatic;

NH—$R_4$ is peptidyl or $R_4$ is independently selected from the group consisting of hydrogen, alkyl, cycloalkyl, aromatic, and heteroaromatic; and non-hydrogen $R_1$, $R_2$, $R_3$, $R_4$, $R_6$, $R_7$, and $R_8$ can independently be substituted with alkylamino, alkoxy, amino, halide, nitro, sulfate, sulfonamide, sulfoxide, or thiol ether, whereby the β-amyloid-associated disease is treated.

2. A method of treating a subject having or at risk of having a β-amyloid-associated disease, comprising:

administering to a subject having or at risk of having Alxheimer disease and free of symptoms otherwise calling for treatment with a compound of Formula IA or Formula IB, a therapeutically effective amount of a compound of Formula IA or Formula IB

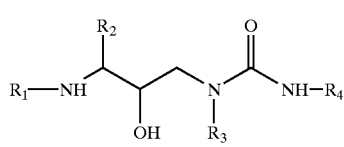
Formula IA

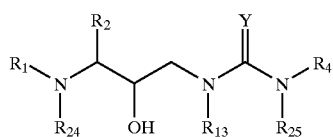
Formula IB wherein, with respect to Formula IA:
(i) $R_2$ is benzyl and $R_1$ is —CO—CH(NHR)CH$_2$CONH$_2$, wherein:
R is carbobenzyloxy, $R_3$ is methyl, and $R_4$ is methyl;
R is carbobenzyloxy, $R_3$ is methyl, and $R_4$ is n-butyl;
R is carbobenzyloxy, $R_3$ is isobutyl, and $R_4$ is methyl;
R is carbobenzyloxy, $R_3$ is isobutyl, and $R_4$ is n-butyl;
R is quinolinyl-2-carboxamide, $R_3$ is isobutyl, and $R_4$ is n-butyl;
R is carbobenzyloxy, $R_3$ is isobutyl, and $R_4$ is n-propyl;
R is carbobenzyloxy, $R_3$ is isobutyl, and $R_4$ is ethyl;
R is carbobenzyloxy, $R_3$ is isobutyl, and $R_4$ is isopropyl;
R is carbobenzyloxy, $R_3$ is isobutyl, and $R_4$ is tert-butyl;
R is quinolinyl-2-carboxamide, $R_3$ is isobutyl, and $R_4$ is tert-butyl;
R is carbobenzyloxy, $R_3$ is isopentyl, and $R_4$ is tert-butyl;
R is quinolinyl-2-carboxamide, $R_3$ is isopentyl, and $R_4$ is tert-butyl;
R is carbobenzyloxy, $R_3$ is $CH_2C_6H_{11}$, and $R_4$ is tert-butyl;
R is quinolinyl-2-carboxamide, $R_3$ is $CH_2C_6H_{11}$, and $R_4$ is tert-butyl;
R is carbobenzyloxy, $R_3$ is benzyl, and $R_4$ is tert-butyl;
R is quinolinyl-2-carboxamide, $R_3$ is benzyl, and $R_4$ is tert-butyl;
R is carbobenzyloxy, $R_3$ is (R)—CH(CH$_3$)-phenyl, and $R_4$ is tert-butyl;
R is carbobenzyloxy, $R_3$ is (S)—CH(CH$_3$)-phenyl, and $R_4$ is tert-butyl;
R is carbobenzyloxy, $R_3$ is CH$_2$(4-pyridyl), and $R_4$ is tert-butyl; or
R is quinolinyl-2-carboxamide, $R_3$ is CH$_2$(4-pyridyl), and $R_4$ is tert-butyl; or
(ii) $R_1$ is —CO—CH(C(CH$_3$)$_3$)NHR, wherein: R is COCH$_2$NHCH$_3$ HCl, $R_2$ is benzyl, $R_3$ is isopentyl, and $R_4$ is tert-butyl;

and, with respect to Formula IB, $R_1$ is a radical represented by any of the formulas A1, A2, A3 below:

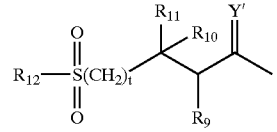
A1

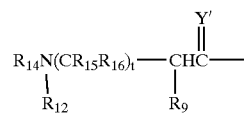
A2

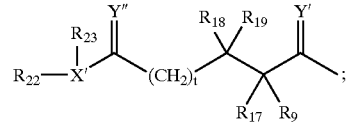
A3

$R_2$ represents alkyl, aryl, cycloalkyl, cycloalkylalkyl and aralkyl radicals, which radicals are optionally substituted with a group selected from —NO$_2$, —OR$_{30}$, —SR$_{30}$, and halogen radicals, wherein $R_{30}$ represents hydrogen and alkyl radicals;

$R_4$ represents radicals represented by the formula

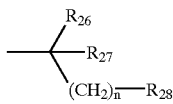

wherein n represents an integer of from 0 to 6, $R_{26}$ and $R_{27}$ independently represent radicals as defined for $R_{13}$ and amino acid side chains selected from the group consisting of valine, isoleucine, glycine, alanine, allo-isoleucine, asparagine, leucine, glutamine, and t-butylglycine or $R_{26}$ and $R_{27}$ together with the carbon atom to which they are attached form a cycloalkyl radical; and $R_{28}$ represents cyano, hydroxyl, alkyl, alkoxy, cycloalkyl, aryl, aralkyl, heterocycloalkyl and heteroaryl radicals and radicals represented by the formulas $C(O)R_{29}$, $CO_2R_{29}$, $SO_2R_{29}$, $SR_{29}$, $CONR_{29}R_{21}$, $OR_{29}$, $CF_3$ and $NR_{29}R_{21}$ wherein $R_{29}$ and $R_{21}$ independently represent hydrogen and radicals as defined for $R_{13}$ or $R_{29}$ and $R_{21}$ together with a nitrogen to which they are attached in the formula $-NR_{29}R_{21}$ represent heterocycloalkyl and heteroaryl radicals;

$R_{24}$ represents hydrogen and alkyl radicals;

$R_{25}$ independently represents hydrogen and radicals as defined by $R_{13}$; and $R_{13}$ represents alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals where said substitutents are selected from alkyl, aryl, aralkyl, cycloalkyl, cycloalkylalkyl, heteroaryl, heteroalkyl, heterocycloalkyl, and heterocycloalkylalkyl radicals or, in the case of a disubstituted aminoalkanoyl radical, said substituents along with the nitrogen atom to which they are attached, form a heterocycloalkyl or a heteroaryl radical;

wherein:

$R_{14}$ represents hydrogen and alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxyalkanoyl, heterocyclylcarbonyl, heterocyclyloxycarbonyl, heterocyclylalkanoyl, heterocyclylalkoxycarbonyl, heteroaralkoxycarbonyl, heteroaryloxycarbonyl, heteroaralkanoyl, heteroaroyl, alkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heteroalkyl and heterocycloalkylalkyl radicals or in the case of a disubstituted aminoalkanoyl radical, said substitutents along with the nitrogen atom to which they are attached form a heterocycloalkyl or heteroaryl radical;

$R_{12}$ represents hydrogen and radicals as defined for $R_{13}$ or $R_{14}$ and $R_{12}$ together with the nitrogen to which they are attached form a heterocycloalkyl or heteroaryl radical or when $R_1$ is A1, $R_{12}$ represents hydrogen, radicals as defined for $R_{13}$ and aralkoxycarbonylalkyl and aminocarbonylalkyl and aminoalkyl radicals wherein said amino group may be mono- or disubstituted with substituents selected from alkyl, aryl, aralkyl, cycloalkyl, cycloalkylalkyl, heteroaryl, heteroaralkyl, heteroalkyl, and heterocycloalkylalkyl radicals;

t represents either 0 or 1;

$R_9$ represents hydrogen, $-CH_2SO_2NH_2$, $-CO_2CH_3$, $-CH_2CO_2CH_3$, $-CONH_2$, $-CH_2C(O)NHCH_3$, $-CH_2C(O)N(CH_3)_2$, $-CONHCH_3$, $-CONH(CH_3)_2$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, allo-isoleucine, tert-leucine, phenylalanine, ornithine, alanine, histidine, norleucine, glutamine, valine, threonine, serine, aspartic acid, beta-cyano alanine, and allo-threonine side chains;

$R_{15}$ and $R_{16}$ independently represent hydrogen and radicals as defined for $R_9$, or one of $R_{15}$ and $R_{16}$, together with $R_9$ and the carbon atoms to which they are attached, represent a cycloalkyl radical;

X' represents O, $C(R_{21})$ where $R_{21}$ represents hydrogen and alkyl radicals and N;

Y, Y' and Y'' independently represent O, S and $NR_{20}$ wherein $R_{20}$ represents hydrogen and radicals as defined for $R_{13}$;

$R_{10}$, $R_{11}$, $R_{17}$, $R_{18}$ and $R_{19}$ represent radicals as defined for $R_9$, or one of $R_9$ and $R_{17}$ together with one of $R_{18}$ and $R_{19}$ and the carbon atoms to which they are attached form a cycloalkyl radical; and $R_{22}$ and $R_{23}$ independently represent hydrogen and radicals as defined for $R_{13}$, or $R_{22}$ and $R_{23}$ together with X' represent cycloalkyl, aryl, heterocyclyl and heteroaryl radicals, provided that when X' is O, $R_{23}$ is absent, whereby the β-amyloid disease is treated.

3. A method of treating a subject having or at risk of having a β-amyloid-associated disease, comprising:

administering to a subject having or at risk of having Alzheimer disease a therapeutically effective amount of a compound of Formula I Formula I

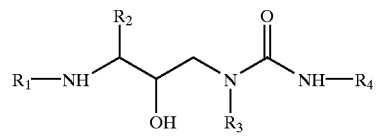

wherein:

$R_1$ is selected from the group consisting of hydrogen, alkyl, cycloalkyl, aromatic, heteroaromatic, acyl $(R_5C=O)$, $R_6O(C=O)$, and $R_7R_8N(C=O)$, wherein $R_5$, $R_6$, $R_7$, and $R_8$ are independently selected from the group consisting of hydrogen, alkyl, cycloalkyl, aromatic, and heteroaromatic;

$R_2$ and $R_3$ are each independently selected from the group consisting of hydrogen, alkyl, cycloalkyl, aromatic, and heteroaromatic;

$NH-R_4$ is peptidyl or $R_4$ is independently selected from the group consisting of hydrogen, alkyl, cycloalkyl, aromatic, and heteroaromatic; R5 is selected from the group consisting of hydrogen, alkyl, cycloalkyl, aromatic, and heteroaromatic; and non-hydrogen $R_1$, $R_2$, $R_3$, $R_4$, and $R_5$ can independently be substituted with alkylamino, alkoxy, amino, halide, nitro, sulfate, sulfonamide, sulfoxide, or thiol ether, excluding compounds in which:

(i) $R_2$ is benzyl and $R_1$ is $-CO-CH(NHR)CH_2CONH_2$, wherein:

R is carbobenzyloxy, $R_3$ is methyl, and $R_4$ is methyl;
R is carbobenzyloxy, $R_3$ is methyl, and $R_4$ is n-butyl;
R is carbobenzyloxy, $R_3$ is isobutyl, and $R_4$ is methyl;
R is carbobenzyloxy, $R_3$ is isobutyl, and $R_4$ is n-butyl;
R is quinolinyl-2-carboxamide, $R_3$ is isobutyl, and $R_4$ is n-butyl;
R is carbobenzyloxy, $R_3$ is isobutyl, and $R_4$ is n-propyl;
R is carbobenzyloxy, $R_3$ is isobutyl, and $R_4$ is ethyl;
R is carbobenzyloxy, $R_3$ is isobutyl, and $R_4$ is isopropyl;
R is carbobenzyloxy, $R_3$ is isobutyl, and $R_4$ is tert-butyl;
R is quinolinyl-2-carboxamide, $R_3$ is isobutyl, and $R_4$ is tert-butyl;
R is carbobenzyloxy, $R_3$ is isopentyl, and $R_4$ is tert-butyl;
R is quinolinyl-2-carboxamide, $R_3$ is isopentyl, and $R_4$ is tert-butyl;
R is carbobenzyloxy, $R_3$ is $CH_2C_6H_{11}$, and $R_4$ is tert-butyl;
R is quinolinyl-2-carboxamide, $R_3$ is $CH_2C_6H_{11}$, and $R_4$ is tert-butyl;
R is carbobenzyloxy, $R_3$ is benzyl, and $R_4$ is tert-butyl;
R is quinolinyl-2-carboxamide, $R_3$ is benzyl, and $R_4$ is tert-butyl;
R is carbobenzyloxy, $R_3$ is (R)—$CH(CH_3)$-phenyl, and $R_4$ is tert-butyl;
R is carbobenzyloxy, $R_3$ is (S)—$CH(CH_3)$-phenyl, and $R_4$ is tert-butyl;
R is carbobenzyloxy, $R_3$ is $CH_2$(4-pyridyl), and $R_4$ is tert-butyl; or
R is quinolinyl-2-carboxamide, $R_3$ is $CH_2$(4-pyridyl), and $R_4$ is tert-butyl;

(ii) $R_1$ is —CO—$CH(C(CH_3)_3)$NHR, wherein: R is $COCH_2NHCH_3$ HCl, $R_2$ is benzyl, $R_3$ is isopentyl, and $R_4$ is tert-butyl; and (iii) $R_1$ is a radical represented by any of the formulas $A_1$, $A_2$, $A_3$ below:

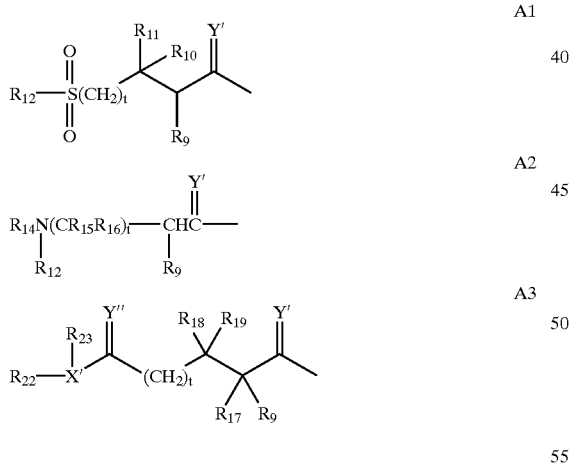

wherein:

$R_{14}$ represents hydrogen and alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxyalkanoyl, heterocyclylcarbonyl, heterocyclyloxycarbonyl, heterocyclylalkanoyl, heterocyclylalkoxycarbonyl, heteroaralkoxycarbonyl, heteroaryloxycarbonyl, heteroaralkanoyl, heteroaroyl, alkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heteroalkyl and heterocycloalkylalkyl radicals or in the case of a disubstituted aminoalkanoyl radical, said substitutents along with the nitrogen atom to which they are attached form a heterocycloalkyl or heteroaryl radical;

$R_{12}$ represents hydrogen and radicals as defined for $R_{13}$ or $R_{14}$ and $R_{12}$ together with the nitrogen to which they are attached form a heterocycloalkyl or heteroaryl radical or when $R_1$ is A1, $R_{12}$ represents hydrogen, radicals as defined for $R_{13}$ and aralkoxycarbonylalkyl and aminocarbonylalkyl and aminoalkyl radicals wherein said amino group may be mono- or disubstituted with substituents selected from alkyl, aryl, aralkyl, cycloalkyl, cycloalkylalkyl, heteroaryl, heteroaralkyl, heteroalkyl, and heterocycloalkylalkyl radicals;

t represents either 0 or 1;

$R_9$ represents hydrogen, —$CH_2SO_2NH_2$, —$CO_2CH_3$, —$CH_2CO_2CH_3$, —$CONH_2$, —$CH_2C(O)NHCH_3$, —$CH_2C(O)N(CH_3)_2$, —$CONHCH_3$, —$CONH(CH_3)_2$, —$(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl radicals and amino acid side chains selected from asparagine, S-methyl cysteine and the corresponding sulfoxide and sulfone derivatives thereof, glycine, leucine, isoleucine, alloisoleucine, tert-leucine, phenylalanine, ornithine, alanine, histidine, norleucine, glutamine, valine, threonine, serine, aspartic acid, beta-cyano alanine, and allo-threonine side chains;

$R_{15}$ and $R_{16}$ independently represent hydrogen and radicals as defined for $R_9$, or one of $R_{15}$ and $R_{16}$, together with $R_9$ and the carbon atoms to which they are attached, represent a cycloalkyl radical;

$R_{13}$ represents alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals where said substitutents are selected from alkyl, aryl, aralkyl, cycloalkyl, cycloalkylalkyl, heteroaryl, heteroalkyl, heterocycloalkyl, and heterocycloalkylalkyl radicals or, in the case of a disubstituted aminoalkanoyl radical, said substituents along with the nitrogen atom to which they are attached, form a heterocycloalkyl or a heteroaryl radical;

X' represents O, $C(R_{21})$ where $R_{21}$ represents hydrogen and alkyl radicals and N;

Y' and Y" independently represent O, S and $NR_{20}$ wherein $R_{20}$ represents hydrogen and radicals as defined for $R_{13}$;

$R_{10}$, $R_{11}$, $R_{17}$, $R_{18}$ and $R_{19}$ represent radicals as defined for $R_9$, or one of $R_9$ and $R_{17}$ together with one of $R_{18}$ and $R_{19}$ and the carbon atoms to which they are attached form a cycloalkyl radical; and $R_{22}$ and $R_{23}$ independently represent hydrogen and radicals as defined for R13, or $R_{22}$ and $R_{23}$ together with X' represent cycloalkyl, aryl, heterocyclyl and heteroaryl radicals, provided that when X' is O, $R_{23}$ is absent, whereby the β-amyloid-associated disease is treated.

* * * * *

UNITED STATES PATENT AND TRADEMARK OFFICE
CERTIFICATE OF CORRECTION

PATENT NO.    : 6,696,488 B2                                          Page 1 of 1
DATED         : February 24, 2004
INVENTOR(S)   : Wolfe, Michael S. and Selkoe, Dennis J.

It is certified that error appears in the above-identified patent and that said Letters Patent is hereby corrected as shown below:

Column 28,
Line 65, please change "β-amyloid-associated disease" to -- Alzheimer's disease --
Line 67, change "Alzheimer disease" to -- Alzheimer's disease --

Column 29,
Lines 34 and 37, please change "β-amyloid-associated disease" to -- Alzheimer's disease --
Line 39, change "Alxheimer disease" to -- Alzheimer's disease --

Column 32,
Line 32, change "β-amyloid disease" to -- Alzheimer's disease --
Line 34, please change "β-amyloid-associated disease" to -- Alzheimer's disease --
Line 36, change "Alzheimer disease" to -- Alzheimer's disease --

Column 34,
Line 65, please change "β-amyloid-associated disease" to -- Alzheimer's disease --

Signed and Sealed this

Twenty-second Day of June, 2004

JON W. DUDAS
*Acting Director of the United States Patent and Trademark Office*